US011123375B2

(12) United States Patent
Xu et al.

(10) Patent No.: US 11,123,375 B2
(45) Date of Patent: Sep. 21, 2021

(54) METHODS OF TREATING TISSUE VOIDS FOLLOWING REMOVAL OF IMPLANTABLE INFUSION PORTS USING ADIPOSE TISSUE PRODUCTS

(71) Applicant: LifeCell Corporation, Madison, NJ (US)

(72) Inventors: Hui Xu, Plainsboro, NJ (US); Carrie Fang, Madison, NJ (US); Mrinal Shah, Parsippany, NJ (US); Israel James Jessop, Annandale, NJ (US)

(73) Assignee: LifeCell Corporation, Madison, NJ (US)

( * ) Notice: Subject to any disclaimer, the term of this patent is extended or adjusted under 35 U.S.C. 154(b) by 8 days.

(21) Appl. No.: 16/502,640

(22) Filed: Jul. 3, 2019

(65) Prior Publication Data
US 2020/0000855 A1 Jan. 2, 2020

(51) Int. Cl.
*A61K 35/35* (2015.01)
*A61K 31/728* (2006.01)
*A61L 27/54* (2006.01)
*C12N 5/077* (2010.01)

(52) U.S. Cl.
CPC ............ *A61K 35/35* (2013.01); *A61K 31/728* (2013.01); *A61L 27/54* (2013.01); *C12N 5/0653* (2013.01); *A61L 2300/412* (2013.01); *A61L 2430/34* (2013.01)

(58) Field of Classification Search
CPC .. A61L 27/3604; A61L 27/56; A61L 2430/40; A61L 2430/34; A61L 27/3633; A61L 27/3683; A61L 27/3687; A61L 27/3691; A61L 27/58; A61L 2400/06
See application file for complete search history.

(56) References Cited

U.S. PATENT DOCUMENTS

| 4,233,969 A | 11/1980 | Lock et al. |
| 4,373,519 A | 2/1983 | Errede et al. |
| 4,569,348 A | 2/1986 | Hasslinger |
| 4,582,640 A | 4/1986 | Smestad et al. |
| 4,703,108 A | 10/1987 | Silver et al. |
| 4,902,508 A | 2/1990 | Badylak et al. |
| 4,950,483 A | 8/1990 | Ksander et al. |
| 4,969,912 A | 11/1990 | Kelman et al. |
| 5,024,841 A | 6/1991 | Chu et al. |
| 5,104,957 A | 4/1992 | Kelman et al. |
| 5,131,850 A | 7/1992 | Brockbank |
| 5,149,331 A | 9/1992 | Ferdman et al. |
| 5,160,313 A | 11/1992 | Carpenter et al. |
| 5,231,169 A | 7/1993 | Constantz et al. |
| 5,254,133 A | 10/1993 | Seid |
| 5,263,971 A | 11/1993 | Hirshowitz et al. |
| 5,275,826 A | 1/1994 | Badylak et al. |
| 5,284,655 A | 2/1994 | Bogdansky et al. |
| 5,298,015 A | 3/1994 | Komatsuzaki et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,437,651 A | 8/1995 | Todd et al. |
| 5,489,304 A | 2/1996 | Orgill et al. |
| 5,549,584 A | 8/1996 | Gross |
| 5,613,982 A | 3/1997 | Goldstein |
| 5,622,867 A | 4/1997 | Livesey et al. |
| 5,632,778 A | 5/1997 | Goldstein |
| 5,636,643 A | 6/1997 | Argenta et al. |
| 5,641,518 A | 6/1997 | Badylak et al. |
| 5,645,081 A | 7/1997 | Argenta et al. |
| 5,728,752 A | 3/1998 | Scopelianos et al. |
| 5,739,176 A | 4/1998 | Dunn et al. |
| 5,834,232 A | 11/1998 | Bishop et al. |
| 5,993,844 A | 11/1999 | Abraham et al. |
| 6,027,743 A | 2/2000 | Khouri et al. |
| 6,071,267 A | 6/2000 | Zamierowski |
| 6,096,347 A | 8/2000 | Geddes et al. |
| 6,135,116 A | 10/2000 | Vogel et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,345,623 B1 | 2/2002 | Heaton et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,553,998 B2 | 4/2003 | Heaton et al. |
| 6,576,265 B1 | 6/2003 | Spievack |

(Continued)

FOREIGN PATENT DOCUMENTS

| EP | 1683417 A1 | 7/2006 |
| EP | 1433423 B1 | 12/2008 |

(Continued)

OTHER PUBLICATIONS

Ahn et al., The past, present, and future of xenotransplantation. Yonsei Med J. Dec. 31, 2004;45(6):1017-24.
Allman et al., Xenogeneic extracellular matrix grafts elicit a TH2-restricted immune response. Transplantation. Jun. 15, 2001;71(11):1631-40.
Argenta et al., Vacuum-assisted closure: a new method for wound control and treatment: clinical experience. Ann Plast Surg. Jun. 1997;38(6):563-76.
Aycock et al., Parastomal hernia repair with acellular dermal matrix. J Wound Ostomy Continence Nurs. Sep.-Oct. 2007;34(5):521-3.
B-Bridge International, Inc., Type 1 Collagenase Assay Kit. Catalog # AK07. www.b-bridge.com. 4 pages (2009).

(Continued)

*Primary Examiner* — Michael B. Pallay
(74) *Attorney, Agent, or Firm* — McCarter & English, LLP; Matthew R. Van Eman

(57) ABSTRACT

Compositions and methods for treating tissue are provided. The compositions may include tissue matrix derived from adipose tissue suitable for injection, small-volume implantation, or use as a soft-tissue regenerative material. Also provided are methods for producing such compositions.

19 Claims, 20 Drawing Sheets

(56) References Cited

U.S. PATENT DOCUMENTS

| | | |
|---|---|---|
| 6,599,318 B1 | 7/2003 | Gabbay |
| 6,613,278 B1 | 9/2003 | Mills et al. |
| 6,666,892 B2 | 12/2003 | Hiles et al. |
| 6,814,079 B2 | 11/2004 | Heaton et al. |
| 6,840,960 B2 | 1/2005 | Bubb |
| 6,933,326 B1 | 8/2005 | Griffey et al. |
| 6,998,418 B1 | 2/2006 | Sung et al. |
| 7,070,584 B2 | 7/2006 | Johnson et al. |
| 7,153,518 B2 | 12/2006 | Wironen et al. |
| 7,198,046 B1 | 4/2007 | Argenta et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,700,819 B2 | 4/2010 | Ambrosio et al. |
| 7,763,769 B2 | 7/2010 | Johnson et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 8,324,449 B2 | 12/2012 | McQuillan et al. |
| 9,375,513 B2 | 6/2016 | Sun et al. |
| 9,532,863 B2 | 1/2017 | Hayzlett |
| 9,782,436 B2 | 10/2017 | Sun |
| 10,314,861 B2 | 6/2019 | Sun |
| 2002/0103542 A1 | 8/2002 | Bilbo |
| 2002/0120185 A1 | 8/2002 | Johnson |
| 2002/0193448 A1 | 12/2002 | Wallace et al. |
| 2003/0035843 A1 | 2/2003 | Livesey et al. |
| 2003/0039678 A1 | 2/2003 | Stone et al. |
| 2003/0104026 A1 | 6/2003 | Wironen et al. |
| 2003/0143207 A1 | 7/2003 | Livesey et al. |
| 2003/0225347 A1 | 12/2003 | Argenta et al. |
| 2004/0037735 A1 | 2/2004 | DePaula et al. |
| 2004/0078077 A1 | 4/2004 | Binette et al. |
| 2005/0028228 A1 | 2/2005 | McQuillan et al. |
| 2005/0043819 A1 | 2/2005 | Schmidt et al. |
| 2005/0125077 A1 | 6/2005 | Harmon et al. |
| 2005/0159822 A1 | 7/2005 | Griffey et al. |
| 2005/0260176 A1 | 11/2005 | Ayares et al. |
| 2006/0058892 A1 | 3/2006 | Lesh et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0210960 A1 | 9/2006 | Livesey et al. |
| 2007/0004961 A1 | 1/2007 | Case et al. |
| 2007/0071729 A1 | 3/2007 | Bernstein |
| 2007/0078522 A2 | 4/2007 | Griffey et al. |
| 2007/0104759 A1 | 5/2007 | Dunn et al. |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0114277 A1 | 5/2008 | Ambrosio et al. |
| 2008/0279824 A1 | 11/2008 | Matheny et al. |
| 2009/0024224 A1 | 1/2009 | Chen et al. |
| 2009/0035289 A1 | 2/2009 | Wagner et al. |
| 2009/0157017 A1 | 6/2009 | Ambrosio |
| 2009/0198167 A1 | 8/2009 | Ambrosio |
| 2009/0220579 A1 | 9/2009 | Hassingboe et al. |
| 2009/0287181 A1 | 11/2009 | Kagan |
| 2009/0306790 A1 | 12/2009 | Sun |
| 2009/0326515 A1 | 12/2009 | Kagan |
| 2010/0021961 A1 | 1/2010 | Fujisato et al. |
| 2010/0040687 A1 | 2/2010 | Pedrozo et al. |
| 2010/0058952 A1 | 3/2010 | Yang et al. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0179515 A1 | 7/2010 | Swain et al. |
| 2010/0209408 A1 | 8/2010 | Livesey et al. |
| 2010/0272782 A1 | 10/2010 | Owens et al. |
| 2011/0020271 A1 | 1/2011 | Niklason et al. |
| 2011/0184357 A1 | 7/2011 | Robinson et al. |
| 2011/0251566 A1 | 10/2011 | Zimnitsky et al. |
| 2012/0010728 A1 | 1/2012 | Sun et al. |
| 2012/0040013 A1 | 2/2012 | Owens et al. |
| 2012/0189588 A1 | 7/2012 | Nahas et al. |
| 2013/0053960 A1 | 2/2013 | Park et al. |
| 2013/0121970 A1 | 5/2013 | Owens et al. |
| 2013/0122068 A1 | 5/2013 | Fermanian et al. |
| 2013/0158676 A1 | 6/2013 | Hayzlett et al. |
| 2013/0280223 A1 | 10/2013 | Owens et al. |
| 2013/0280801 A1 | 10/2013 | Sun |
| 2016/0235892 A1 | 8/2016 | Detamore et al. |
| 2016/0271295 A1 | 9/2016 | Sun et al. |
| 2017/0224869 A1* | 8/2017 | Shah .................. A61L 27/56 |
| 2018/0353644 A1 | 12/2018 | Sun et al. |
| 2019/0076582 A1 | 3/2019 | Connor |
| 2019/0111183 A1 | 4/2019 | Xu et al. |
| 2019/0117833 A1 | 4/2019 | Xu et al. |
| 2019/0262394 A1 | 8/2019 | Sun |
| 2020/0114091 A1 | 4/2020 | Xu et al. |

FOREIGN PATENT DOCUMENTS

| | | |
|---|---|---|
| WO | 1990/00060 A1 | 1/1990 |
| WO | 1998/44809 A1 | 10/1998 |
| WO | 1999/32049 A1 | 7/1999 |
| WO | 1999/65470 A1 | 12/1999 |
| WO | 2000/016822 A1 | 3/2000 |
| WO | 2000/047114 A1 | 8/2000 |
| WO | 2002/40630 A2 | 5/2002 |
| WO | 2003/017826 A2 | 3/2003 |
| WO | 2003/032735 A1 | 4/2003 |
| WO | 2005/009134 A1 | 2/2005 |
| WO | 2005/120597 A1 | 12/2005 |
| WO | 2007/043513 A1 | 4/2007 |
| WO | 2007/134134 A2 | 11/2007 |
| WO | 2008/134305 A2 | 11/2008 |
| WO | 2009/009620 A2 | 1/2009 |
| WO | 2010/019753 A2 | 2/2010 |
| WO | 2010/078353 A2 | 7/2010 |
| WO | 2011/019822 A2 | 2/2011 |
| WO | 2012/142419 A1 | 10/2012 |
| WO | 2012/166784 A1 | 12/2012 |
| WO | 2017/029633 A1 | 2/2017 |

OTHER PUBLICATIONS

Badylak et al., Endothelial cell adherence to small intestinal submucosa: an acellular bioscaffold. Biomaterials. Dec. 1999;20(23-24):2257-63.

Badylak et al., Extracellular matrix as a biological scaffold material: Structure and function. Acta Biomater. Jan. 2009;5(1):1-13.

BC BioLibrary, Sectioning of OCT Embedded Tissue. Retrieved online at: http://www.bcbiolibrary.icapture.ubc.ca/pathologists-researchers/docs/BL.LAB.GN.002.01%20Sectioning%20of%20OCT%20Embedded%20Tissue.pdf. 4 pages, (2008).

Beniker et al., The use of acellular dermal matrix as a scaffold for periosteum replacement. Orthopedics. May 2003;26(5 Suppl):s591-6.

Blackburn et al., Negative-pressure dressings as a bolster for skin grafts. Ann Plast Surg. May 1998;40(5):453-7.

Brandi et al., Treatment with vacuum-assisted closure and cryo-preserved homologous de-epidermalised dermis of complex traumas to the lower limbs with loss of substance, and bones and tendons exposure. J Plast Reconstr Aesthet Surg. Dec. 2008;61(12):1507-11.

Bruder et al., The effect of implants loaded with autologous mesenchymal stem cells on the healing of canine segmental bone defects. J Bone Joint Surg Am. Jul. 1998;80(7):985-96.

Buma et al., Tissue engineering of the meniscus. Biomaterials. Apr. 2004;25(9):1523-32.

(56) References Cited

OTHER PUBLICATIONS

Chaplin et al., Use of an acellular dermal allograft for dural replacement: an experimental study. Neurosurgery. Aug. 1999;45(2):320-7.
Chariker et al., Effective management of incisional and cutaneous fistulae with closed suction wound drainage. Contemporary Surgery. Jun. 1989;34:59-63.
Chen et al., Acellular collagen matrix as a possible "off the shelf" biomaterial for urethral repair. Urology. Sep. 1999;54 (3):407-10.
Chinn et al., Closed wound suction drainage. J Foot Surg. Jan.-Feb. 1985;24(1):76-81.
Choi et al., Decellularized extracellular matrix derived from human adipose tissue as a potential scaffold for allograft tissue engineering. J Biomed Mater Res A. Jun. 1, 2011;97(3):292-9.
Choi et al., Fabrication of porous extracellular matrix scaffolds from human adipose tissue. Tissue Eng Part C Methods. Jun. 2010;16(3):387-96.
Collins et al., Cardiac xenografts between primate species provide evidence for the importance of the alpha-galactosyl determinant in hyperacute rejection. J Immunol. May 15, 1995;154(10):5500-10.
Costantino et al., Human dural replacement with acellular dermis: clinical results and a review of the literature. Head Neck. Dec. 2000;22(8):765-71.
Dagalakis et al., Design of an artificial skin. Part III. Control of pore structure. J Biomed Mater Res. Jul. 1980;14 (4):511-28.
Dattilo et al., Medical Textiles: Application of an Absorbable Barbed Bi-directional Surgical Suture. Journal of Textile and Apparel, Technology and Management. 2002 Spring;2(2):1-5.
Defranzo et al., Vacuum-assisted closure for the treatment of abdominal wounds. Clin Plast Surg. Apr. 2006;33 (2):213-24.
Dobrin et al., Elastase, collagenase, and the biaxial elastic properties of dog carotid artery. Am J Physiol. Jul. 1984;247(1 Pt 2):H124-31.
Ducksters, Chemistry for Kids, Chemical Mixtures. Retrieved online at: http://www.ducksters.com/science/chemistry/chemical_mixtures.php, 1 page, retrieved Nov. 10, 2015.
Edel, The use of a connective tissue graft for closure over an immediate implant covered with occlusive membrane. Clin Oral Implants Res. Mar. 1995;6(1):60-5.
Flack et al., An economic evaluation of VAC therapy compared with wound dressings in the treatment of diabetic foot ulcers. J Wound Care. Feb. 2008;17(2):71-8.
Fowler et al., Ridge Preservation Utilizing an Acellular Dermal Allograft and Demineralized Freeze-Dried Bone Allograft: Part II. Immediate Endosseous Impact Placement. J Periodontol. Aug. 2000;71(8):1360-1364.
Fowler et al., Root coverage with an acellular dermal allograft: a three-month case report. J Contemp Dent Pract. Aug. 15, 2000;1(3):47-59.
Galili et al., Interaction between human natural anti-alpha-galactosyl immunoglobulin G and bacteria of the human flora. Infect Immun. Jul. 1988;56(7)1730-7.
Galili et al., Man, apes, and Old World monkeys differ from other mammals in the expression of alpha-galactosyl epitopes on nucleated cells. J Biol Chem. Nov. 25, 1988;263(33):17755-62.
Galili, Interaction of the natural anti-Gal antibody with alpha-galactosyl epitopes: a major obstacle for xenotransplantation in humans. Immunol Today. Oct. 1993;14(10):480-2.
Gamba et al., Experimental abdominal wall defect repaired with acellular matrix. Pediatr Surg Int. Sep. 2002;18 (5-6):327-31.
Gebhart et al., A radiographical and biomechanical study of demineralized bone matrix implanted into a bone defect of rat femurs with and without bone marrow. Acta Orthop Belg. 1991;57(2):130-43.
Griffey et al., Particulate dermal matrix as an injectable soft tissue replacement material. J Biomed Mater Res. 2001;58(1)10-5.
Hammond et al., Parastomal hernia prevention using a novel collagen implant: a randomised controlled phase 1 study. Hernia. Oct. 2008;12(5):475-81.

Ju et al., Beneficial effect of hydrophilized porous polymer scaffolds in tissue-engineered cartilage formation. J Biomed Mater Res B Appl Biomater. Apr. 2008;85(1):252-60.
Kay et al., Guided bone regeneration: integration of a resorbable membrane and a bone graft material. Pract Periodontics Aesthet Dent. Mar. 1997;9(2):185-94.
KCI Licensing, Inc., V.A.C.® Therapy Safety Information. 4 pages, (2007).
Kish et al., Acellular dermal matrix (AlloDerm): new material in the repair of stoma site hernias. Am Surg. Dec. 2005;71 (12):1047-50.
Kridel et al., Septal perforation repair with acellular human dermal allograft. Arch Otolaryngol Head Neck Surg. Jan. 1998;124(1):73-8.
Laidlaw et al., Tympanic membrane repair with a dermal allograft. Laryngoscope. Apr. 2001;111(4 Pt 1):702-7.
Lee et al., In vitro evaluation of a poly(lactide-co-glycolide)-collagen composite scaffold for bone regeneration. Biomaterials. Jun. 2006;27(18):3466-72.
Lu et al., Novel porous aortic elastin and collagen scaffolds for tissue engineering. Biomaterials. Oct. 2004;25 (22):5227-37.
Marzaro et al., Autologous satellite cell seeding improves in vivo biocompatibility of homologous muscle acellular matrix implants. Int J Mol Med. Aug. 2002;10(2):177-82.
Masters, Reliable, inexpensive and simple suction dressings. Br J Plast Surg. Apr. 1998;51(3):267.
O'Brien et al., The effect of pore size on cell adhesion in collagen-GAG scaffolds. Biomaterials. Feb. 2005;26 (4):433-41.
O'Connor et al., Vacuum-assisted closure for the treatment of complex chest wounds. Ann Thorac Surg. Apr. 2005;79(4):1196-200.
Parnigotto et al., Experimental defect in rabbit urethra repaired with acellular aortic matrix. Urol Res. Jan. 2000;28 (1):46-51.
Randall et al., Use of an acellular regenerative tissue matrix in combination with vacuum-assisted closure therapy for treatment of a diabetic foot wound. J Foot Ankle Surg. Sep.-Oct. 2008;47(5):430-3.
Reddy et al., Regeneration of functional bladder substitutes using large segment acellular matrix allografts in a porcine model. J Urol. Sep. 2000;164(3 Pt 2):936-41.
Simon et al., Early failure of the tissue engineered porcine heart valve Synergraft in pediatric patients. Eur J Cardiothorac Surg. Jun. 2003;23(6):1002-6.
Suckow et al., Enhanced bone regeneration using porcine small intestinal submucosa. J Invest Surg. Sep.-Oct. 1999;12(5):277-87.
Wei et al., Construction of varying porous structures in acellular bovine pericardia as a tissue-engineering extracellular matrix. Biomaterials. May 2005;26(14):1905-13.
Wu et al., An Injectable Adipose Matrix for Soft Tissue Reconstruction. Plastic and Reconstructive Surgery Advance Online Article. DOI: 10.1097/PRS.0b013e31824endc. 33 pages, (2012).
Wu et al., Preparation of collagen-based materials for wound dressing. Chin Med J (Engl). Mar. 2003;116(3):419-23.
Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.
Yang et al., A cartilage ECM-derived 3-D porous acellular matrix scaffold for in vivo cartilage tissue engineering with PKH26-labeled chondrogenic bone marrow-derived mesenchymal stem cells. Biomaterials. May 2008;29(15):2378-87.
Zhao et al., The study of the feasibility of segmental bone defect repair with tissue-engineered bone membrane: a qualitative observation. Strategies Trauma Limb Reconstr. Sep. 2008;3(2):57-64.
Zheng et al., Porcine small intestine submucosa (SIS) is not an acellular collagenous matrix and contains porcine DNA: possible implications in human implantation. J Biomed Mater Res B Appl Biomater. Apr. 2005;73(1):61-7.

\* cited by examiner

NO CELLS BY H&E
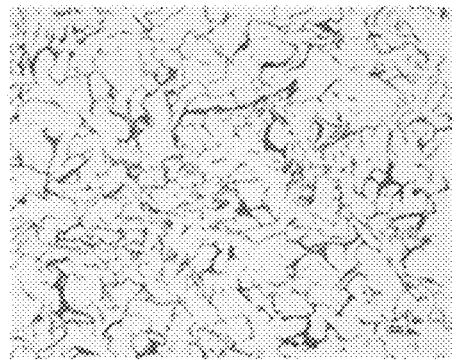
FIG. 8A
|  | NATIVE FAT | PROCESSED ADIPOSE |
|---|---|---|
| RESIDUAL DNA (µg/mg) | 300 | 50 |
| OIL (%) | 100 | 8 |
FIG. 8B
NEGATIVE FOR MHC-I&II
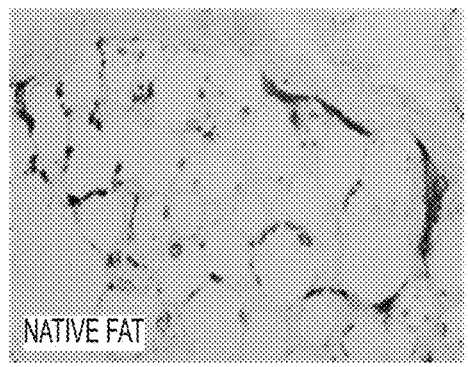
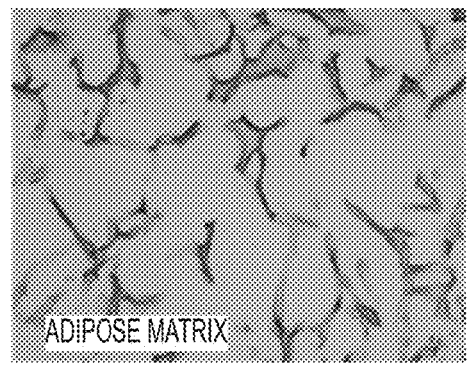
THE TISSUE PRODUCT RETAINED MAJOR MATRIX COMPONENTS OF NATIVE FAT
FIG. 8C

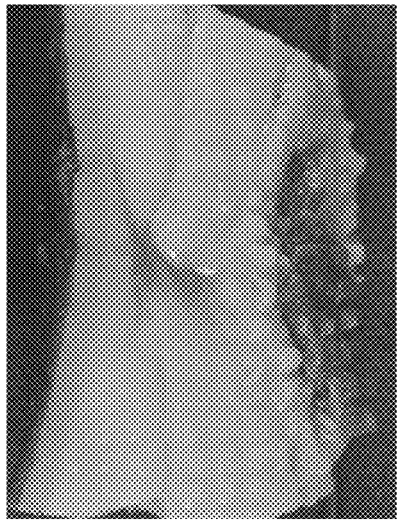
FIG. 21B
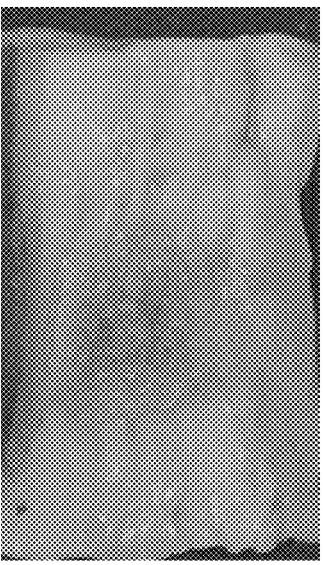
FIG. 21D
FIG. 21A
FIG. 21C

FIG. 22A  EMPTY DEFECT 14 DAYS
FIG. 22B  28 DAYS
FIG. 22C  ADIPOSE MATRIX 14 DAYS
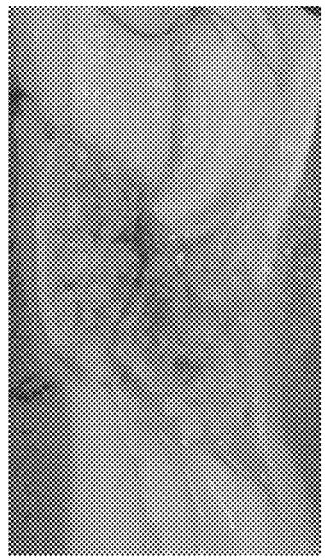
FIG. 22D  28 DAYS

METHODS OF TREATING TISSUE VOIDS FOLLOWING REMOVAL OF IMPLANTABLE INFUSION PORTS USING ADIPOSE TISSUE PRODUCTS

The present disclosure relates generally to methods to prevent complications arising from removal of objects or tissue from soft tissues. Specifically, the disclosures herein relate to methods of preventing complications arising from removal of implantable infusion ports or other implantable devices from a soft tissue. The methods can include use of a flowable adipose-derived acellular tissue matrix composition.

The use of totally implantable intravenous infusion ports has become widespread since the introduction of the device in the 1980's. Infusion ports are used extensively in a variety of clinical situations that require long-term reliable central venous access. Some examples include delivery of chemotherapeutic medications to cancer patients, administration of total parenteral nutrition, and other indications.

Although removal of the implantable infusion port is generally safe and straightforward, complications can occur. An extremely common complication is an accumulation of tissue fluid—a seroma—in the "dead space" left in the subcutaneous fat following removal of the port. Seromas usually resolve spontaneously over six-to-eight weeks without treatment. Uncommonly a seroma may become large and/or infected and require aspiration or open (surgical) drainage.

More commonly, however, the seroma is experienced by the patient as a hard, tender subcutaneous "lump." In addition to local tenderness, which usually persists for two months or more, the lump is a source of concern and anxiety for the patient—particularly, the cancer patient. Also, as the seroma is gradually resorbed by the body over time, healing may leave a firm or hard subcutaneous scar that may take years to resolve. Moreover, as the scar tissue contracts, the overlying skin is pulled downward to create a pronounced concavity in the skin, leaving a noticeable deformity.

In cases where no seroma forms following removal of the infusion port, a soft tissue defect nonetheless may result from removal, lysis during manipulation, and compression of fat tissue during the insertion procedure. This localized loss of fat volume can leave a retracted, crater-like deformity of the overlying skin that is no longer supported by subcutaneous fat.

Obliteration of the dead space left following removal of an infusion port would greatly decrease the incidence of or prevent seroma formation. Replacement of fat volume would support the overlying skin and prevent development a visible deformity arising from skin tissue unsupported by underlying fat in a localized area.

Currently available means to prevent formation of soft tissue dead space have remained essentially unchanged for decades. Such means include suturing the walls of the dead space together, drain placement to facilitate egress of blood and serous fluid from the dead space, and external compression to obliterate the dead space. These methods are only marginally effective, however, and have associated problems. For example, drains exiting through the skin or incision are uncomfortable and require care to maintain patency and prevent drain-related infections. Suturing the dead space creates a deformity of the surrounding soft tissue, moreover, the sutures are foreign bodies which increase the risk of wound infection. Constant external compression of the wound site is cumbersome and often painful.

Accordingly, there exists a need for a safe, effective means for preventing a soft-tissue dead space following removal of a mass from soft tissue, including an implantable port. Filling of the soft tissue dead space at the time of or after surgical removal of a mass occupying the soft tissue with a flowable adipose tissue matrix is such a means.

The present disclosure also provides methods of using compositions comprising an acellular adipose tissue matrix to eliminate a dead space at the time of or after removal of a soft tissue mass. In some embodiments, the steps include removing an implanted infusion port form an anatomic location of a subject to create a void; and delivering a flowable composition comprising an adipose-based tissue matrix into the void at t time proximate to the removing step. The composition is delivered into the soft tissue defect at a time proximate to the removing step.

Compositions comprising a flowable adipose acellular tissue matrix are described, and such compositions are suitable for small-volume treatment or injection. The compositions and methods described herein allow for filling of a soft tissue defect, wherein the subcutaneous dead space is filled with a volume flowable acellular adipose tissue matrix and the skin incision is closed, whereby the flowable acellular adipose tissue matrix is contained within the soft tissue dead space. As the skin and subcutaneous wounds heal, the recipient subject's own adipocytes and other cells including vascular endothelial cells, periadipocytes, and fibroblasts colonize the flowable acellular adipose tissue matrix to form new adipose tissue. These cells produce collagen, glycoproteins, and other components as the flowable acellular adipose tissue matrix is re-modeled and fully incorporated into the recipient subject's own adipose tissue.

The present disclosure provides methods for repairing a skin deformity comprising making a skin incision proximate to a deformity; dividing subcutaneous scar tissue to release skin attached to the scar tissue, creating a dead space; injecting a flowable composition containing an adipose-based tissue matrix into the dead space; and closing the skin incision.

The present disclosure also provides compositions for injection, small-volume implantation, or filling of larger voids or adding volume with adipose-based tissue products. The disclosure also provides methods for producing such compositions.

The present disclosure provides methods for producing an injectable product from adipose tissue matrix. The method may include selecting an adipose tissue; mechanically processing the adipose tissue to reduce the tissue size; treating the mechanically processed tissue to remove substantially all cellular material from the tissue; suspending the tissue in a solution to form a suspension; treating the suspension to produce a stabilized three-dimensional structure with a micro-porous structure; and mechanically processing the stabilized three-dimensional structure to produce particles.

The present disclosure also provides tissue product compositions. The compositions may include a particulate tissue matrix, wherein the tissue product composition comprises an adipose acellular tissue matrix that has been formed into a porous sponge and then formed into the particulate, and wherein the particulate tissue matrix comprises particles having a longest dimension between about 0.05 mm and 3 mm.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 8A is a hematoxylin and eosin ("H&E") stained section of adipose tissue matrix material produced according to the disclosed Examples;

FIG. 8B is a table of DNA and lipid content measurement for adipose tissue produced according to the disclosed Examples;

FIG. 8C is an immune-stained portion of adipose tissue matrix material, negative for MHC-1 & II staining as compared to a native fat control, produced according to the disclosed Examples;

FIGS. 21A-D illustrates gross images of an acute wound model with or without implantation of an adipose tissue matrix composition; and FIGS. 22A-D illustrates gross images of a chronic wound model with or without implantation of an adipose tissue matrix composition.

DETAILED DESCRIPTION OF CERTAIN EXEMPLARY EMBODIMENTS

Figure 1:
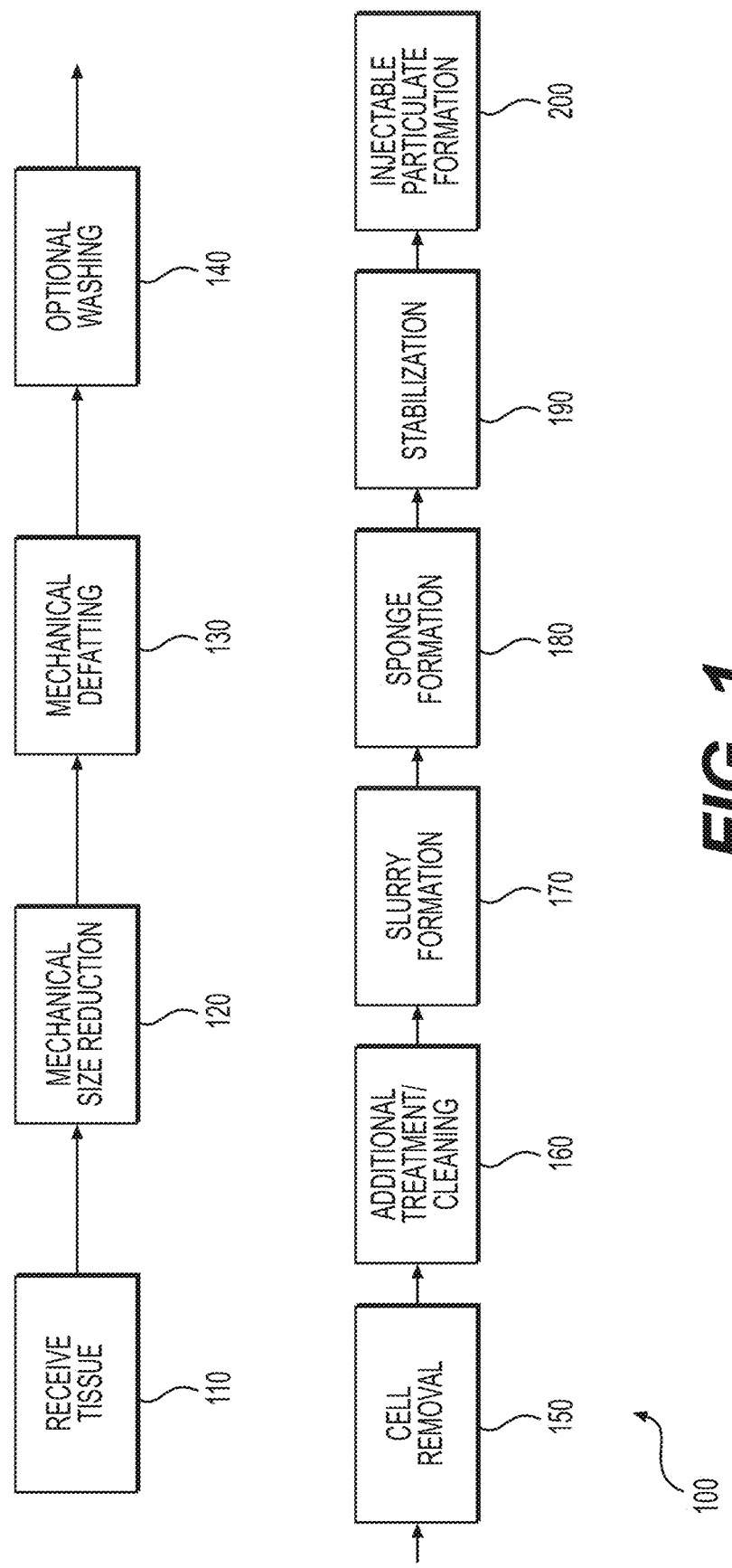
FIG. 1 is a flow chart outlining a process for producing an adipose tissue matrix sponge, according to embodiments of the present disclosure.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains an extracellular matrix protein. "Tissue products" may include acellular or partially decellularized tissue matrices, as well as decellularized tissue matrices that have been repopulated with exogenous cells.

As used herein, the term "acellular tissue matrix" refers to an extracellular matrix derived from human or animal tissue, wherein the matrix retains a substantial amount of natural collagen and glycoproteins needed to serve as a scaffold to support tissue regeneration. "Acellular tissue matrices" are different from the purified collagen materials, such as acid-extracted purified collagen, which are substantially void of other matrix proteins and do not retain the natural microstructural features of tissue matrix due to the purification processes. Although referred to as "acellular tissue matrices," it will be appreciated that such tissue matrices may be combined with exogenous cells, including, for example, stem cells, or cells from a patient in whom the "acellular tissue matrices" may be implanted. A "decellularized adipose tissue matrix" will be understood to refer to an adipose-based tissue from which all cells have been removed to produce adipose extracellular matrix. "Decellularized adipose tissue matrix" can include intact matrix or matrix that has been further processed as discussed herein, including mechanical processing, formation of a sponge, and/or further processing to produce particulate matrix.

"Acellular" or "decellularized" tissue matrices will be understood to refer to tissue matrices in which no cells are visible using light microscopy.

"Adipose tissue," as used herein, relates to any number of fat-containing tissues, including subcutaneous fat, fat pads, breast tissue, and the like.

Removal of a mass from soft tissue creates a dead space, as discussed. For example, removal of an implantable tissue port from the subcutaneous tissue of the chest wall creates a dead space that often leads to seroma formation, which the patient may experience as a painful, anxiety-provoking lump. Where no seroma forms, removal of the implantable port can create a volume defect in the subcutaneous fat that is manifest as a depression deformity in the overlying skin.

Various human and animal tissues may be used to produce products for a dead space to prevent complications and skin deformity following removal of a mass from soft tissue. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products may include, for example, acellular tissue matrices, tissue allografts or xenografts, and/or reconstituted tissues (i.e., at least partially decellularized tissues that have been seeded with cells to produce viable materials).

A variety of tissue products have been produced for treating soft and hard tissues. For example, ALLODERM® and STRATTICE™ (LIFECELL CORPORATION, BRANCHBURG, N.J.) are two dermal acellular tissue matrices made from human and porcine dermis, respectively. Although such materials are very useful for treating certain types of conditions, materials having different biological and mechanical properties may be desirable for certain applications. For example, ALLODERM® and STRATTICE™ have been used to assist in the treatment of structural defects and/or to provide support to tissues (e.g., for abdominal walls or in breast reconstruction), and their strength and biological properties make them well suited for such uses. However, such materials may not be ideal for regeneration, repair, replacement, and/or augmentation of adipose-containing tissues, when the desired result is production of adipose tissue with viable adipocytes. Accordingly, the present disclosure provides tissue products that are useful for the treatment of a tissue defects/imperfections involving adipose-containing tissues, such as a dead space in the subcutaneous fat following removal of an implantable injection port. The present disclosure also provides methods for producing these tissue products.

The tissue products may include adipose tissues that have been processed to remove at least some of the cellular components. In some cases, all, or substantially all cellular materials are removed, thereby leaving adipose extracellular matrix proteins. In addition, the products may be processed to remove some or all of the extracellular and/or intracellular lipids. In some cases, however, complete removal of extracellular and/or intracellular lipids can be damaging to the architecture and functions of the adipose matrix. For example, adipose tissues that are chemically or enzymatically treated for an extended period of time may have denatured or otherwise damaged collagen, or may be depleted of proteins needed for adipose regeneration. Accordingly, in some cases, the product contains a certain level of residual lipids. The remaining lipid content can be, for example, about 5%, 6%, 7%, 8%, 9%, or 10% by weight of the product. As described further below, the extracellular matrix proteins may be further treated to produce a three-dimensional porous, or sponge-like material, and the porous or sponge-like material may be further processed to produce an injectable product.

As noted, the tissue products of the present disclosure are formed from adipose tissues. The adipose tissues may be derived from human or animal sources. For example, human adipose tissue may be obtained from cadavers. In addition, human adipose tissue could be obtained from live donors (e.g., with autologous tissue). Adipose tissue may also be obtained from animals such as pigs, monkeys, or other sources. If animal sources are used, the tissues may be further treated to remove antigenic components such as 1,3-alpha-galactose moieties, which are present in pigs and other mammals, but not humans or primates. See Xu, Hui, et al., "A Porcine-Derived Acellular Dermal Scaffold that Supports Soft Tissue Regeneration: Removal of Terminal Galactose-$\alpha$-(1,3)-Galactose and Retention of Matrix Structure," Tissue Engineering, Vol. 15, 1-13 (2009), which is hereby incorporated by reference in its entirety. In addition, the adipose tissue may be obtained from animals that have been genetically modified to remove antigenic moieties.

Figure 2:
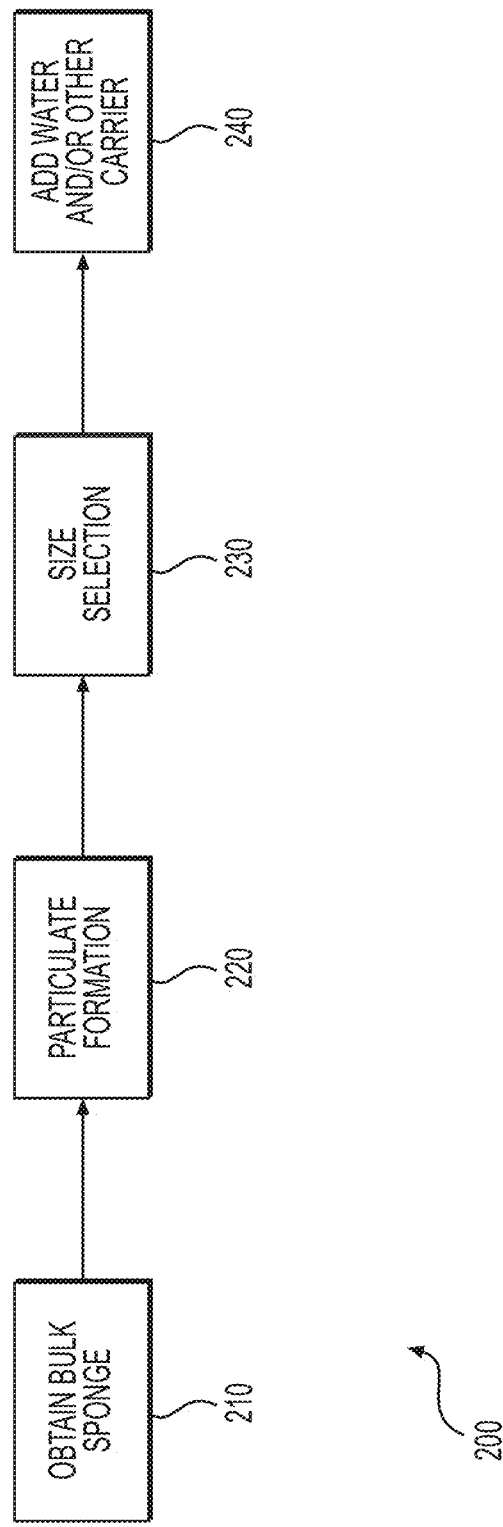
FIG. 2 is a flow chart outlining a process for producing an injectable adipose tissue matrix product, according to embodiments of the present disclosure.

An exemplary process for producing the tissue products of the present disclosure is illustrated in FIGS. 1 and 2. FIG. 1 provides a flow chart illustrating the basic steps that may be used to produce a suitable adipose tissue sponge, which can then be further processed to produce injectable or implantable particulate. As shown, the process may include a number of steps, but it will be understood that additional or alternative steps may be added or substituted depending on the particular tissue being used, desired application, or other factors.

As shown, the process 100 may begin generally at Step 110, wherein tissue is received. The tissue may include a variety of adipose tissue types, including, for example, human or animal adipose tissue. Suitable tissue sources may include allograft, autograft, or xenograft tissues. When xenografts are used, the tissue may include adipose from animals including porcine, cow, dog, cat, domestic or wild sources, and/or any other suitable mammalian or non-mammalian adipose source.

The tissue may be harvested from animal sources using any desirable technique, but may be generally obtained using, if possible, aseptic or sterile techniques. The tissue may be stored in cold or frozen conditions or may be immediately processed to prevent any undesirable changes due to prolonged storage.

After receiving the tissue, the tissue may initially be subject to mechanical size reduction at Step 120 and/or mechanical defatting at Step 130. Mechanical size reduction may include gross or large cutting of tissue using manual blades or any other suitable grinding process.

Mechanical defatting at Step 130 may be important in the production of tissue. Specifically, to assist in lipid removal, the adipose may be subject to a variety of mechanical processing conditions. For example, the mechanical processing may include grinding, blending, chopping, grating, or otherwise processing the tissue. The mechanical processing may be performed under conditions that allow for a certain degree of heating, which may assist in liberating or removing lipids. For example, the mechanical processing may be performed under conditions that may allow the adipose tissue to heat up to 122° F. (50° C.). The application of external heat may be insufficient to release the lipids; therefore, heat generated during mechanical disruption may be preferred to assist in lipid removal. In some examples, heating during mechanical processing may be a pulse in temperature rise and may be short in duration. This heat pulse may cause liquefaction of lipid released from broken fat cells by mechanical disruption, which may then cause efficient phase separation for bulk lipid removal. In an example, when processing a porcine adipose tissue, the temperature reached during this process is above 100° F. and may not exceed 122° F. (50° C.). The range of temperature reached can be adjusted according to the origin of the adipose tissue. For example, the temperature can be further lowered to about 80° F., 90° F., 100° F., 110° F., or 120° F. when processing less-saturated tissues, e.g., primate tissues. Alternatively, the process may be selected to ensure the adipose reaches a minimum temperature such as 80° F., 90° F., 100° F., 110° F., or 120° F.

In some cases, the mechanical defatting may be performed by mechanically processing the tissue with the addition of little or no washing fluids. For example, the tissue may be mechanically processed by grinding or blending without the use of solvents. Alternatively, when grinding the tissue requires moisture, for example to increase flowability or decrease viscosity, water may be used, including pure water or saline or other buffers including saline or phosphate buffered saline. In some examples, the tissue may be processed by adding a certain quantity of solvent that is biocompatible, such as saline (e.g., normal saline, phosphate buffered saline, or solutions including salts and/or detergents). Other solutions that facilitate cell lysis may also be appropriate, including salts and/or detergents.

After mechanical processing and lipid removal, the adipose may be washed at Step 140. For example, the tissue may be washed with one or more rinses with various biocompatible buffers. For example, suitable wash solutions may include saline, phosphate buffered saline, or other suitable biocompatible materials or physiological solutions. In an example, water may be used as a rinsing agent to further break the cells, after which phosphate buffered saline, or any other suitable saline solution, may be introduced to allow the matrix proteins to return to biocompatible buffers.

The washing may be performed along with centrifugation or other processes to separate lipids from the tissue. For example, in some embodiments, the material is diluted with water or another solvent. The diluted material is then centrifuged, and free lipids will flow to the top, while the extracellular matrix proteins are deposited as a pellet. The protein pellet may then be resuspended, and the washing and centrifugation may be repeated until a sufficient amount of the lipids are removed.

After any washing, the adipose may be treated to remove some or all cells from the adipose tissue as indicated at Step 150. The cell removal process may include a number of suitable processes. For example, suitable methods for removing cells from the adipose tissue may include treatment with detergents such as deoxycholic acid, polyethylene glycols, or other detergents at concentrations and times sufficient to disrupt cells and/or remove cellular components.

After cell removal, additional processing and/or washing steps may be incorporated, depending on the tissue used or ultimate structure desired, as indicated at Step 160. For example, additional washing or treatment may be performed to remove antigenic materials such as alpha-1,3-galactose moieties, which may be present on non-primate animal tissues. In addition, during, before, and/or after the washing steps, additional solutions or reagents may be used to process the material. For example, enzymes, detergents, and/or other agents may be used in one or more steps to further remove cellular materials or lipids, remove antigenic materials, and/or reduce the bacteria or other bioburden of the material. For example, one or more washing steps may be included using detergents, such as sodium dodecylsulfate or Triton to assist in cell and lipid removal. In addition, enzymes such as lipases, DNAses, RNAses, alpha-galactosidase, or other enzymes may be used to ensure destruction of nuclear materials, antigens from xenogenic sources, residual cellular components and/or viruses. Further, acidic solutions and/or peroxides may be used to help further remove cellular materials and destroy bacteria and/or viruses, or other potentially infectious agents.

After removal of lipids and cellular components, the material may then be formed into a porous or sponge-like material. Generally, the extracellular matrix is first resuspended in an aqueous solvent to form a slurry-like material as indicated at Step 170. A sufficient amount of solvent is used to allow the material to form a liquid mass that may be poured into a mold having the size and shape of the desired tissue product. The amount of water or solvent added may be varied based on the desired porosity of the final material. In some cases, the slurry-like material may have a solid concentration of about 2% to about 10% by weight, preferably about 2% to about 5%. In some cases, the resuspended extracellular matrix may be mechanically treated by grinding, cutting, blending or other processes one or more additional times, and the treated material may be centrifuged and resuspended one or more times to further remove cellular material or lipids (if needed) and/or to control the viscosity of the extracellular matrix.

Figure 3:
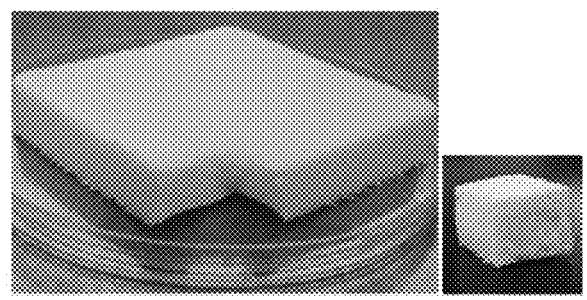
FIG. 3 illustrates a bulk piece of adipose tissue matrix sponge produced according to various embodiments.

Once any additional washing and grinding steps are complete, the resuspended material is placed in a container or mold to form the porous, sponge-like product, as indicated at Step 180. Generally, the porous or sponge-like material is formed by drying the material to leave a three-dimensional matrix with a porous structure. In some embodiments, the material is freeze-dried. Freeze-drying may allow production of a three-dimensional structure that generally conforms to the shape of the mold, as shown in FIG. 3. The specific freeze drying protocol may be varied based on the solvent used, sample size, and/or to optimize processing time. One suitable freeze-drying process may include cooling the material to −10° C. over a 20-40 minute period; holding the samples at −10° C. for 120-180 minutes and further cooling the sample to −40° C. to insure complete freezing; applying a vacuum; raising the temperature to −5° C. and holding for 30-60 hours; raising the temperature to 25° C. and holding for 6-12 hours. The freeze-dried samples may then be removed from the freeze-dryer and packaged in foil pouches under nitrogen.

After formation of a solid or sponge, the material may optionally be stabilized, as indicated at Step 190. In some cases, the stabilization may include additional processes such as cross-linking, treatment with dehydrothermal (DHT)

processes, or other suitable stabilization methods. For example, generally, a mechanically processed tissue, when formed into a porous matrix, may form a more putty- or paste-like material when it is implanted in a body, becomes wet, or is placed in a solution. Therefore, the desired shape and size may be lost. In addition, the porous structure, which may be important for supporting cell attachment, tissue growth, vascular formation, and tissue regeneration, may be lost. Accordingly, the material may be further processed to stabilize the size, shape, and structure of the material.

In some embodiments, the material is cross-linked for stabilization. In some embodiments, the material is cross-linked after freeze drying. However, the material could also be cross-linked before or during the freeze-drying process. Cross-linking may be performed in a variety of ways. In one embodiment, cross-linking is accomplished by contacting the material with a cross-linking agent such as glutaraldehyde, genepin, carbodiimides (e.g., 1-ethyl-3-(3-dimethyl-aminopropyl) carbodiimide hydrochloride (EDC)), and diisocyantes. In addition, cross-linking may be performed by heating the material in a vacuum. For example, in some embodiments, the material may be heated to between 70° C. to 120° C., or between 80° C. and 110° C., or to about 100° C., or any values between the specified ranges in a reduced pressure or vacuum. In addition, other cross-linking processes, or combination of processes may be used to produce any of the disclosed products, including ultraviolet irradiation, gamma irradiation, and/or electron beam irradiation. In addition, a vacuum is not needed but may reduce cross-linking time. Further, lower or higher temperatures could be used as long as melting of the matrix proteins does not occur and/or sufficient time is provided for cross-linking.

In various embodiments, the cross-linking process may be controlled to produce a tissue product with desired mechanical, biological, and/or structural features. For example, cross-linking may influence the overall strength of the material, and the process may be controlled to produce a desired strength. In addition, the amount of cross-linking may affect the ability of the product to maintain a desired shape and structure (e.g., porosity) when implanted. Accordingly, the amount of cross-linking may be selected to produce a stable three-dimensional shape when implanted in a body, when contacted with an aqueous environment, and/or when compressed (e.g., by surrounding tissues or materials).

Excessive cross-linking may change the extracellular matrix materials. For example, excessive cross-linking may damage collagen or other extracellular matrix proteins. The damaged proteins may not support tissue regeneration when the tissue products are placed in an adipose tissue site or other anatomic location. In addition, excessive cross-linking may cause the material to be brittle or weak. Accordingly, the amount of cross-linking may be controlled to produce a desired level of stability, while maintaining desired biological, mechanical, and/or structural features.

Exemplary cross-linking processes may include contacting a freeze-dried material, produced as discussed above, with glutaraldehyde or EDC. For example, a 0.1% glutaraldehyde solution may be used, and the tissue may be submerged in the solution for about for 18 hours followed by extensive rinsing in water to remove the solution. Alternatively, or in combination, a dehydrothermal (DHT) process may be used. For example, one exemplary dehydrothermal process includes treating the material at 100° C. and ~20 inches of Hg for 18 hours, followed by submersion in water. The final cross-linked tissue products may be stored in a film pouch.

After formation of a solid or sponge, the tissue product may then be further processed to produce an injectable form. An exemplary process for forming an injectable form is illustrated by Process 200, as shown in FIG. 2. It will be understood that "injectable" may include materials injected with a syringe, cannula, or needle, but the disclosed material can be produced having sizes and mechanical properties suitable for other modes of administration, including manual insertion (e.g., with a hand or other bulk instrument such as a spatula, tube, or other device equipped to handle flowable materials).

The process for producing the injectable begins by obtaining the bulk sponge, as indicated at Step 210. Obtaining the bulk sponge may be performed using the process described with reference to FIG. 1, or suitable variations thereof. In one aspect of the present disclosure, the process may start with stable (porcine or human) adipose tissue matrix sponges.

After the bulk sponge material is obtained, the material may be subject to size reduction or particulate formation, as indicated at Step 220. The size reduction or particulate formation may include mechanical cutting, grinding, or blending to produce particulates of a desired size and size distribution. In some aspects of the present disclosure, when the initial material is a dry sponge, grinding may be preferred to reduce the dry sponge to smaller particles. Size reduction may be performed at room temperature.

Notably, it has been discovered that reduction of the sponge size should be done to maintain the porous sponge structure within the particles. As such, the particles should be large enough to maintain the sponge structure in order to support adipogenesis. Loss or lack of the porous structure can result in a composition that does not support adipose growth. For example, the particles may be formed from a sponge such that the particles have a size of at least 0.5 microns, 1 micron, 2 microns, 3 microns, 4 microns, or more. The particle size may be selected based on the sponge microstructure.

With continuing reference to FIG. 2, in a next Step 230, a size selection may be desired. For example, a stabilized sponge, once ground or otherwise treated to produce particles, may then be sieved or otherwise sorted to obtain a desired size of particles as flowable/injectable adipose tissue matrix material. In some examples, one or more injectable adipose tissue matrix sponges with distinct particle sizes may be desired to accommodate different needle sizes. In this case, the material is sieved to achieve preferred particle size ranges. In an embodiment, particle sizes may range from 50 microns to 2,800 microns. For example, the ground sponge may be sieved to retrieve particles with the following preferred dimensions: Fine particles (e.g., 50-100 microns); Medium particles (e.g., 0.4 mm to 0.6 mm); Large particles (e.g., 0.8 mm to 1 mm); and Larger particles (e.g., 2.8 mm to 3.4 mm). In some aspects of the present disclosure, particle sizes in this range may not invoke a varied biological response. In other words, for example, there may be no difference in biological responses with particle sizes ranging from 50 microns to 3,400 microns. Different applications that may require a specific size of an injection needle may select a specific size of particle(s) without the need to consider if the biological responses will be different. Furthermore, in some cases, larger particles are used to increase volume retention, whereas smaller particles may be used when a smaller injection device is desired.

Once the size of the particle is selected, at a next Step 240, the particles may be hydrated and/or added to another carrier to a desired degree to produce flowability and desired degree of solid content. For example, the sieved particles may be hydrated with saline or other material(s) to result in a solid concentration of 5-12%. In addition, other carriers may be used or added, including hyaluronic-acid based materials (e.g., JUVEDERM®, ALLERGAN, or similar materials). In some other examples, the particles may be hydrated using water, saline, phosphate buffered saline, or any other suitable physiological solution. In some examples of the present disclosure, Step 240 may be performed before Step 230, in that, the particles may be hydrated or added to a carrier before a size selection is made and/or before the particles are sieved.

Figure 4:
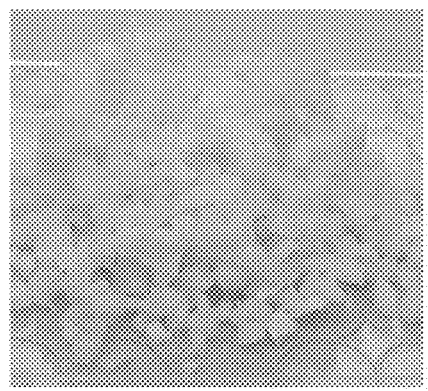
FIG. 4 is an enlarged view of a particulate tissue matrix having dimensions between 2 and 3 mm after being produced by milling an adipose tissue matrix sponge.
Figure 5:
FIG. 5 illustrates a group of acellular tissue matrix particulates produced by milling or fracturing an adipose tissue matrix sponge to produce particles between 100 and 300 microns (μm), and a paste/pudding-like injectable material after its hydration.

Exemplary particulate materials are illustrated in FIGS. 4 and 5. FIG. 4 is an enlarged view of a particulate tissue matrix having dimensions between 2 and 3 mm after being produced by milling an adipose tissue matrix sponge; FIG. 5 illustrates a group of acellular tissue matrix particulates produced by milling or fracturing an adipose tissue matrix sponge to produce particles between 100 and 300 microns, and a paste/pudding-like injectable material after its hydration;

According to certain aspects of this disclosure, a material with a desired tissue matrix solid content may be used. For example, a material that is 5% to 12% solid may be used, and a material that is 7.5-10% is desired. In another example, a material that is 5% to 10% solid may use a suitable carrier to facilitate injection and to prevent particle dissipation away from the injection site. The suitable carrier can be a flowable carrier, e.g. a flowable hyaluronic acid carrier. In some examples, the hyaluronic acid carrier is a non-cross-linked hyaluronic acid carrier. In some other examples, the hyaluronic acid carrier is a cross-linked hyaluronic acid carrier.

As used herein, a "hyaluronic acid based material" is a material comprising hyaluronic acid (HA). HA refers to hyaluronic acid and can also refer to any salts thereof, including, but not limited to, sodium hyaluronate, potassium hyaluronate, magnesium hyaluronate, calcium hyaluronate, and combinations thereof. Both HA and pharmaceutically acceptable salts thereof can be included in the hyaluronic acid based material. Exemplary HA based materials are commercially sold as JUVEDERM® and JUVEDERM VOLUMA®. It should be appreciated that the hyaluronic acid based material may include additional agents such as, for example, lidocaine.

All numbers herein expressing "molecular weight" of HA are to be understood as indicating the weight average molecular weight (Mw) in Daltons.

The molecular weight of HA is calculated from an intrinsic viscosity measurement using the following Mark Houwink relation: Intrinsic Viscosity (m3/kg)=$9.78\times10^{-5}\times Mw^{0.690}$. The intrinsic viscosity is measured according to the procedure defined European Pharmacopoeia (HA monograph No 1472, January 2009).

High molecular weight HA as used herein describes a HA material having a molecular weight of at least about 1.0 million Daltons (Mw≥$10^6$ Da or 1 MDa) to about 4.0 MDa. High molecular weight HA that may be incorporated in the present tissue product compositions may have a molecular weight in the range about 1.5 MDa to about 3.0 MDa, or the high molecular weight HA may have a weight average molecular weight of about 2.0 MDa. In another example, the high molecular weight HA may have a molecular weight of about 3.0 MDa.

Low molecular weight HA as used herein describes a HA material having a molecular weight of less than about 1.0 MDa. Low molecular weight HA can have a molecular weight of between about 200,000 Da (0.2 MDa) to less than 1.0 MDa, for example, between about 300,000 Da (0.3 MDa) to about 750,000 Da. (0.75 MDa), up to but not exceeding 0.99 MDa. Preferably, there is no overlap between the molecular weight distribution of the low and high molecular weight HA materials. Preferably, the mixture of the low molecular weight HA and high molecular weight HA has a bimodal molecular weight distribution. The mixture may also have a multi-modal distribution.

In one aspect of the invention, the adipose tissue product compositions comprise HA having a high molecular weight component and a low molecular weight component, and the high molecular weight component may have a weight average molecular weight at least twice the weight average molecular weight of the low molecular weight component. For example, the molecular weight ratio of the high molecular weight HA to the low molecular weight HA in the composition may be at least 2:1. For example, a tissue product composition may include an HA having a low molecular weight component having a weight average molecular weight of about 500,000 Da, and a high molecular weight component having a weight average molecular weight of about, or at least about, 1.0 MDa. In another example, a tissue product composition in accordance with the invention may include an HA having a low molecular weight component having a weight average molecular weight of about 800,000 Da, and a high molecular weight component having a weight average molecular weight of about, or at least about, 1.6 MDa. It should be appreciated that many different types of HA may be incorporated in the adipose tissue product composition, and the foregoing examples are not intended to be limiting.

In some exemplary embodiments, the HA may be cross-linked using one or more suitable crosslinking agents. The crosslinking agent may be any agent known to be suitable for crosslinking polysaccharides and their derivatives via their hydroxyl groups. Suitable crosslinking agents include but are not limited to, 1,4-butanediol diglycidyl ether (or 1,4-bis(2,3-epoxypropoxy)butane or 1,4-bisglycidyloxybutane, all of which are commonly known as BDDE), 1,2-bis(2,3-epoxypropoxy)ethylene, 1-(2,3-epoxypropyl)-2,3-epoxycyclohexane, and 1-ethyl-3-(3-dimethylaminopropyl) carbodiimide hydrochloride (commonly known as EDC). Other suitable hyaluronan crosslinking agents include multifunctional PEG-based crosslinking agents like pentaerythritol tetraglycidyl ether (PETGE), divinyl sulfone (DVS), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis(sulfosuccinimidyl)suberate (BS), hexamethylenediamine (HMDA), 1-(2,3-epoxypropyl)-2,3-epoxycyclohexane, or combinations thereof.

In one exemplary embodiment of an adipose tissue product composition formed in accordance with the present invention, the adipose tissue product composition includes a flowable carrier comprising a hyaluronic acid based material and a plurality of adipose tissue matrix particles mixed with the carrier. In some exemplary embodiments, the flowable carrier comprises HA that has not been mixed with additional agents; in other exemplary embodiments, the flowable carrier comprises HA mixed with additional agents. Additional agents may include, but are not limited to, anesthetic agents for example, aminoamide local anesthetic and salts thereof or an aminoester local anesthetic and salts thereof. For example, procaine, chloroprocaine, cocaine, cyclomethycaine, cimethocaine, propoxycaine, procaine, proparacaine, tetracaine, or salts thereof, or any combination thereof. In some embodiments, anesthetic agents may comprise articaine, bupivacaine, cinchocaine, etidocaine, levobupivacaine, lidocaine, mepivacaine, piperocaine, prilocaine, ropivacaine, trimecaine, or salts thereof, or any combination thereof.

The flowable carrier may initially be in the form of a flowable liquid solution that can be mixed with the adipose matrix particles to form a slurry. The formed slurry can then be loaded into a syringe or other injection device for administration to a patient. In some exemplary embodiments, the flowable carrier may be a non-crosslinked HA in an amount sufficient to provide improved injectability of the adipose tissue product composition. In some exemplary embodiments, the flowable carrier may be a cross-linked HA in an amount sufficient to provide improved injectability of the adipose tissue product composition. While the flowable carrier is described herein as comprising HA, it is contemplated that other glycosaminoglycans (GAGs) may be utilized as the flowable carrier, such as HSGAG, CSGAG, and/or keratin sulfate type GAGs.

While direct surgical implantation through an open incision is a suitable option for implanting adipose tissue matrix materials to repair certain areas of the body, including a soft tissue defect following removal of an implantable injection port or other soft tissue mass, injection may be preferred for some applications. Particulating the adipose tissue matrix was found to be an improvement for application and injection, compared to applying the adipose tissue matrix in its natural form, but it was found that even particulated pure adipose tissue matrix was not easily applied or injected into a patient. Particularly, application of the particulated tissue matrix material was found to be difficult to control, due to the tendency of the particulated tissue matrix material to spread or aggregate after storage. Further, the injection force required to inject particulated adipose tissue matrix was found to be relatively high and it was found to be relatively difficult to inject all of the particulated tissue matrix loaded into an injection device, such as a syringe.

To address some of the previously described problems of injecting adipose tissue matrix materials, exemplary embodiments described herein provide tissue product compositions including adipose tissue matrix particles mixed within a flowable carrier comprising a hyaluronic acid based material. The formed tissue product composition can be more easily applied than pure adipose tissue matrix particles, as will be described further herein, while maintaining characteristics that encourage tissue growth in the implantation and/or injection area.

In one exemplary embodiment, the adipose tissue matrix particles and flowable carrier may be mixed in a large volume batch under generally sterile conditions to form a tissue product composition in accordance with the present invention. The mixing may comprise, for example, stirring the adipose tissue matrix particles and flowable carrier together to form a slurry. The parameters and technique of the mixing may be altered according to the properties of the flowable carrier and the acellular tissue matrix particles, as well as the general amounts of each in the tissue product composition, and can be readily derived by one skilled in the art from routine experimentation.

To formulate the tissue product compositions in accordance with the present invention, different types of hyaluronic acid based materials could be used. In some cases, all types of HA are initially in a solution having a concentration of 20 mg HA/mL. Exemplary HA types include HA Type 1, HA Type 2, HA Type 3, and HA Type 4. HA Type 1 is a non-crosslinked hyaluronic acid having a G' value of 320 Pa; HA Type 2 and HA Type 3, in contrast, are hyaluronic acids that were cross-linked with an EDC cross-linking agent with different G' and G" values, depending on the degree of cross-linking. HA Type 2 had a G' value of 160 Pa and HA Type 3 had a G' value of between 500-550. HA Type 4 is also cross-linked. HA Type 4 may have a G' value of 350 Pa.

Various hyaluronic acid based materials may be mixed with adipose tissue matrix particles to produce various tissue product compositions described in Table 1 below. It should be appreciated that the hyaluronic acid based materials described herein are exemplary only, and other hyaluronic acid based materials may be mixed with the adipose tissue matrix particles. Further, the compositions given in Table 1 are exemplary only, and other formulations of tissue product compositions may be formed in accordance with the present invention.

TABLE 1

| Composition | Adipose Tissue Matrix Slurries | Adipose Matrix:HA Ratio | HA Type | [HA] (20 mg/mL) | [Adipose Tissue Matrix] (mg/mL) |
|---|---|---|---|---|---|
| 1 | Adipose Tissue Matrix Slurry | 9:1 | HA1 | 2 | 90 |
| 2 | Adipose Tissue Matrix Slurry | 9:1 | HA4 | 2 | 90 |
| 3 | Adipose Tissue Matrix Slurry | 4:1 | HA1 | 4 | 80 |
| 4 | Adipose Tissue Matrix Slurry | 4:1 | HA4 | 4 | 80 |

Turning now to Table 1, exemplary embodiments of tissue product compositions formed in accordance with the present invention are described. Compositions 1-4, representing various tissue product compositions are illustrated in Table 1, but it should be appreciated that other tissue product compositions may be formed in accordance with the present invention. For each Composition 1-4, the adipose tissue matrix particles originated from porcine fat tissue and, when combined with the flowable carrier, produced adipose tissue matrix slurries, which may also be referred to as "flowable adipose tissue matrix." Prior to mixing with the flowable carrier, which was provided in a concentration of 20 mg HA/mL, the adipose tissue matrix particles were in a concentration of 100 mg/mL in an aqueous buffer. As should be appreciated from Table 1, a ratio of Adipose Matrix:HA can be adjusted to produce slurries with varying flow properties, as will be described further herein. It should be understood that the ratios described herein can be either by volume or by mass; in the exemplary embodiments shown in Table 1, the ratio is given as volume Adipose Matrix:volume HA. As exemplified by Compositions 1 and 2, the ratio of Adipose Matrix:HA can be 9:1; and as exemplified by Compositions 3 and 4, the ratio of Adipose Matrix:HA can be 4:1. It should be appreciated that the previously described ratios are exemplary only, and other exemplary embodiments of tissue product compositions may have other ratios of Adipose Matrix:HA including any values between the disclosed ratios.

According to certain aspects of this disclosure, a tissue product composition with a desired tissue matrix particle solid content may be used. For example, a material that is 5% to 15% solid content, such as 7.5% to 10% solid content, may be desired depending on what type of hyaluronic acid based material is mixed with the tissue matrix particles. In some exemplary embodiments, the tissue product composition has 10% solid content, corresponding to 100 mg/mL, of acellular adipose matrix particles.

As discussed above, the tissue products should have the ability to support cell ingrowth and tissue regeneration when implanted in or on a patient. In addition, the tissue products should have the ability to act as a carrier for and support the growth of cells, including stem cells, such as adipose-derived stem cells. Accordingly, the processes discussed above should not alter the extracellular matrix proteins in an unacceptable way (e.g., by damaging protein structure and/or removing important glycosaminoglycans and/or growth factors). In some embodiments, the products will have normal collagen banding as evidenced by high-resolution microscopy, such as transmission electron microscopy or atomic force microscopy, for example.

In various embodiments, the tissue products are treated with a process that retains either or both of the native hyaluronic acid and chondroitin sulfate. Accordingly, the tissue products may include either or both of hyaluronic acid and chondroitin sulfate. In addition, the process may be selected to maintain native growth factors. For example, the tissue products may be produced such that the tissue products contain one or more growth factors selected from PECAM-1, HGF, VEGF, PDGF-BB, follistatin, IL-8, and FGF-basic.

Adipose tissue matrix may be rich in Type IV and Type VI collagens. The ratio between these two types of collagens relative to Type I collagen may be different from a dermal matrix, which may be important factors used to discern adipose matrix from a dermal one, in vivo.

The tissue products described herein may be used to treat a variety of different anatomic sites. For example, as discussed throughout, the tissue products of the present disclosure are produced from adipose tissue matrices. Accordingly, it is believed that the adipose tissue products will provide superior regenerative capabilities when implanted in certain tissue sites, as compared to materials produced from other tissue types. In some cases, the tissue products may be implanted in tissue sites that are predominantly or significantly adipose tissue. In some cases, the tissue products may be used as facial fillers, e.g., to treat lines, wrinkles, voids, or divots, to add volume, or replace lost tissues. In some cases, the tissue sites may include a breast (e.g., for augmentation, replacement of resected tissue, or placement around an implant). In addition, any other adipose-tissue containing site may be selected. For example, the tissue products may be used for reconstructive or cosmetic use in the face, buttocks, abdomen, hips, thighs, or any other site where additional adipose tissue having structure and feel similar to native adipose may be desired. In any of those sites, the tissue may be used to reduce or eliminate wrinkles, sagging, or undesired shapes.

When used for breast tissue replacement or augmentation, the tissue may provide advantages over other tissue products. For example, although some tissue products allow ingrowth and tissue formation, those products may form significant fibrotic tissue that does not mimic normal breast texture and feel, and appears abnormal on radiologic imaging. Since the tissue products of the present disclosure are formed from adipose, they may support more normal regeneration of adipose tissue.

Further, the tissue products may be used as carriers for cells. For example, the products may be implanted in any of the sites or used as discussed above, but may also be seeded with cells. In some cases, the cells may include stem cells such as adipose-derived stem cells. In addition, other pluripotent cells may be use, as well as cells from any tissue source (e.g., blood, bone marrow, fetal stem cells, cord blood cells, etc.) The cells may be seeded onto the tissue after implantation or before implantation. In addition, the cells may be cultured on the tissue product before implantation and then be implanted in or on a body.

As discussed, the particulate tissue matrix product can further comprise a flowable carrier to facilitate the injection of the tissue products. In various embodiments, the particulate tissue matrix and the flowable carrier are packaged in separate containers and are not in contact until being mixed immediately prior to injection. For example, the particulate tissue matrix and the flowable carrier are packaged in separate barrels of a multi-barrel syringe and are mixed shortly before or when the contents are being injected. In other embodiments, the particulate tissue matrix and the flowable carrier are pre-mixed and packaged together. The materials may be separately dried or stored in biocompatible buffers that preserve the biologic properties of the tissue matrix and/or carrier, prevent bacterial growth, or prevent damage during sterilization or storage.

It is to be understood that the "composition" as used in the methods described below may include any of the flowable compositions comprising an adipose-derived tissue matrix product described herein above.

For example, in some embodiments, the adipose-based tissue matrix is in the form of a suspension of tissue particles having a longest dimension no greater than about 3.0 mm. In some embodiments, the adipose-based tissue matrix is in the form of a suspension of tissue particles having a longest dimension of at least 0.05 mm. In some embodiments, the adipose-based tissue matrix is in the form of a suspension of tissue particles having a longest dimension between about 100 µm and about 300 µm. In some embodiments, the adipose-based tissue matrix is in the form of a suspension of tissue particles having a longest dimension between about 50 µm and about 100 µm.

In some embodiments, the composition comprises a carrier preventing dissipation of or otherwise migration of the adipose-based tissue matrix away from the void. In some embodiments, the composition further comprises a glycosaminoglycan. In some embodiments, the glycosaminoglycan is a hyaluronic acid. In some embodiments, the hyaluronic acid is a crosslinked hyaluronic acid. In some embodiments, the hyaluronic acid is a non-crosslinked hyaluronic acid. In some embodiments, the hyaluronic acid is present in the composition at a concentration by weight of about 2.5%.

In some embodiments, the composition comprises a local anesthetic.

Figure 18:
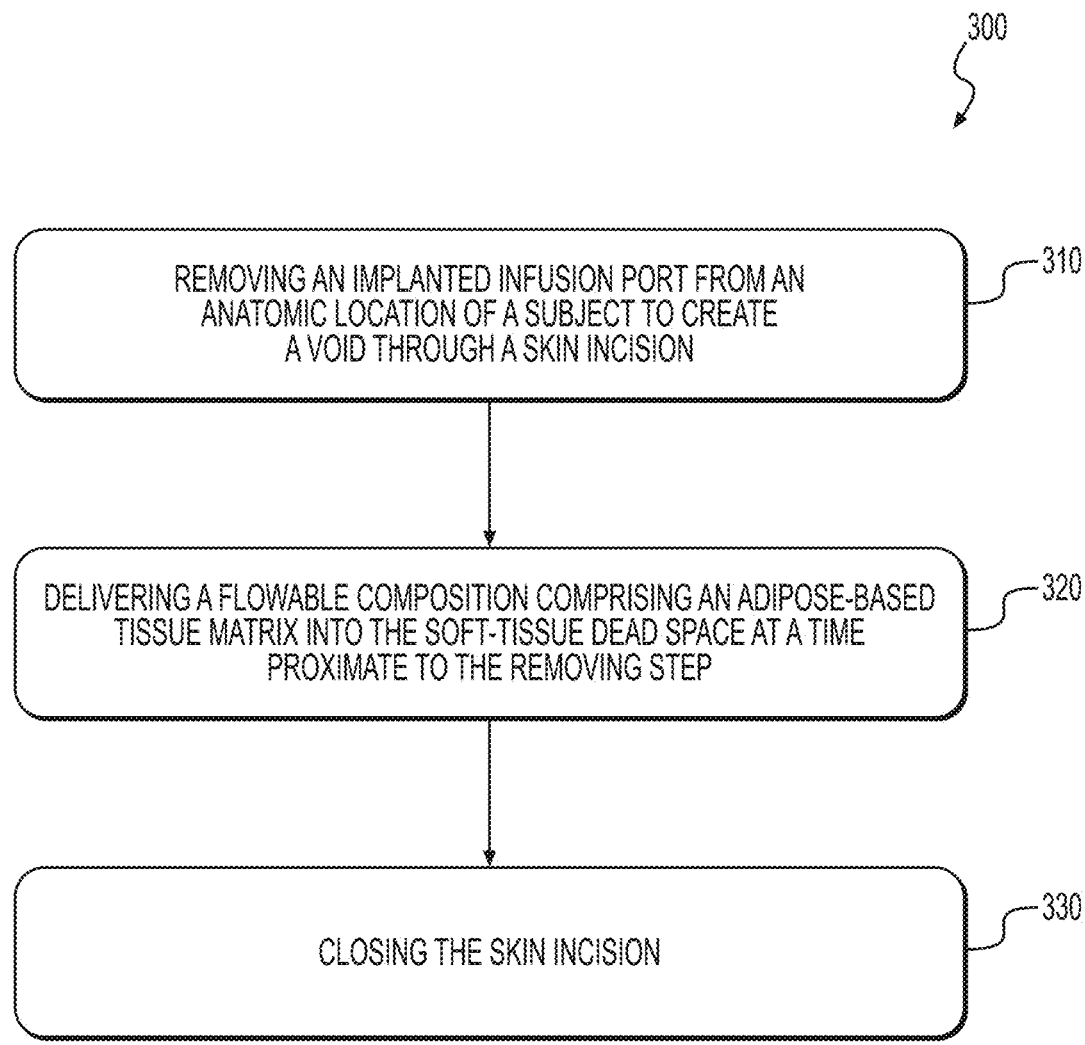
FIG. 18 is a flowchart outlining a process for creating and repairing a soft tissue void using a flowable adipose-based tissue matrix, according to embodiments of the present disclosure.

FIG. 18 is a flowchart outlining a process for creating and repairing a soft tissue void using a flowable adipose-based tissue matrix. FIG. 18 shows a method 300 for treating a void in a soft tissue. Method 300 comprises a removing step 310, a delivering step 320, and a closing step in some embodiments.

Removing step 310 comprises removing an implanted infusion port or other implanted device from an anatomic location of a subject to create a void through a skin incision. The anatomic location is most commonly on the anterior chest wall over the upper (superior) aspect of the pectoralis major muscle. Less commonly, the anatomic location is on the lateral chest wall, the anterior shoulder area, the supraclavicular fossa, the lateral neck, the anterior thigh, and the anterior lower abdomen. These anatomic locations are described by way of example. The actual anatomic location will depend on the site of the implantable port and is not meant to be limiting.

Typically, removing the infusion port involves making a skin incision to expose the implanted port, which is usually immediately below the skin and partially encapsulated in a thin, fibrous capsule. One or more sutures securing the port to the underlying fascia or muscle are cut and also removed. The intravenous catheter is pulled out as one unit with the port. As the intravenous port is removed from the subclavian vein, pressure is held through the wound against the inferior aspect of the clavicle to ensure hemostasis at the catheter exit site of the vein for several minutes. In some embodiments, removing step 310 also comprises excision of any fibrous capsule that may be present. Hemostasis is achieved to prevent post-removal hematoma formation.

Delivering step 320 is performed following removing step 310. In some embodiments, delivering step 320 comprises delivering a flowable composition comprising an adipose-based tissue matrix into the void at a time proximate to the removing step. Use of a flowable composition allows particles of the adipose-based tissue matrix to be distributed throughout all areas of the void created by removal of the implantable port, regardless of the shape of the void. Being fluid-like, the flowable composition will take the shape of the surrounding void.

The delivery step may be performed during the removal procedure or at a later time. For example, the delivery can be performed before closure of the skin incision. Alternatively, the delivery can be performed at a later time if a defect such as a depression forms. In the latter case, delivery may be percutaneous or by producing a new incision.

The flowable composition may be delivered in a variety of ways, in some embodiments. For, example, in some embodiments, a syringe fitted with a needle is used to dispense the composition from the syringe through the needed into the void. The needle may be a 14 gauge ("G"), a 16 G, an 18 G, or a 20 G needle, for example. In some embodiments, the needle is fitted with a cannula, such as an intravenous infusion cannula. In some embodiments, the cannula has a larger bore than a 14 G cannula. In some embodiments, the cannula is a 14 G cannula, a 16 G cannula, an 18 G cannula, a 20 G cannula, or a 21 G cannula. In some embodiments, the cannula has a smaller bore than a 21 G cannula. In some embodiments, a syringe without a needle is used to dispense the composition comprising the adipose-based tissue matrix into the void. In some embodiments, the syringe is fitted with a tube or tube-like device configures to dispense a flowable material. In other embodiments, an instrument other than a syringe is used to position the composition by manual insertion into the void, such as a spatula, a spoon, or the like. The spatula, spoon, or similar instrument is used to place the composition into the void and push the composition, which has a putty-like consistency, in some embodiments, into the depths and side recesses of the cavity, filling the void and eliminating any residual dead space in the soft tissue. In some embodiments, a hand is used to deliver the composition by manual insertion.

The volume of the composition comprising a flowable acellular adipose tissue matrix should completely fill the void, in order to prevent leaving a dead space. It is also important to prevent any visible deformity of the overlying skin that results from inadequate subcutaneous volume and support. The composition comprising a flowable acellular adipose tissue matrix, however, generally loses a small percentage of its volume as the acellular adipose tissue matrix is incorporated into the subject's soft tissue. To offset this volume loss, method steps include delivery of a volume of the flowable adipose tissue matrix generally equal to or slightly greater than the volume of the removed implantable port, or other removed soft tissue mass. In some embodiments, the delivered volume of the flowable adipose tissue matrix is about 95% to about 100% of the volume of the removed mass. In some embodiments, the delivered volume of the flowable adipose tissue matrix is about 100% to about 105% of the volume of the removed mass. In some embodiments, the delivered volume of the flowable adipose tissue matrix is about 105% to about 110%; about 110% to about 115%; about 115% to about 120%; about 120% to about 130%; about 130% to about 135%; about 135% to about 140%; about 140% to about 145%; about 145% to about 150%; or greater than about 150% of the volume of the removed mass.

Closing step 330, in some embodiments, comprises closing the incision. Closing step 330 may be performed, by example, by using an available closing means known in the art, including but not limited to suturing or stapling the skin edges together. Dermal adhesives designed for skin closures, such as those containing cyanoacrylate and other polyacrylate compounds used as medical adhesives, may also or alternatively be used. Regardless of the specific means used to close the skin incision, it is important to achieve a fluid-tight closure, both to facilitate aesthetic healing of the incision and to prevent the adipose-based tissue matrix material from leaking form the void through the improperly closed skin incision.

In some embodiments, it may be desirable to perform closing step 330 before delivering step 320. For example, following hemostasis after completing removing step 310, closing step 330 is performed to close the incision and "seal" the wound. The unsupported skin overlying the void created during removing step 310 will be seen to "sag." Delivering step 320 is then performed by injecting the flowable composition through a needle inserted percutaneously until the skin overlying the void is fully supported, preferably with a slight excess rise above the surrounding skin to allow for volume loss as the adipose-based tissue matrix becomes incorporated in the patient's subcutaneous adipose tissue. By closing the incision before injecting the composition, no composition leaks out through the incision site before or during closing step 330.

Figure 19:
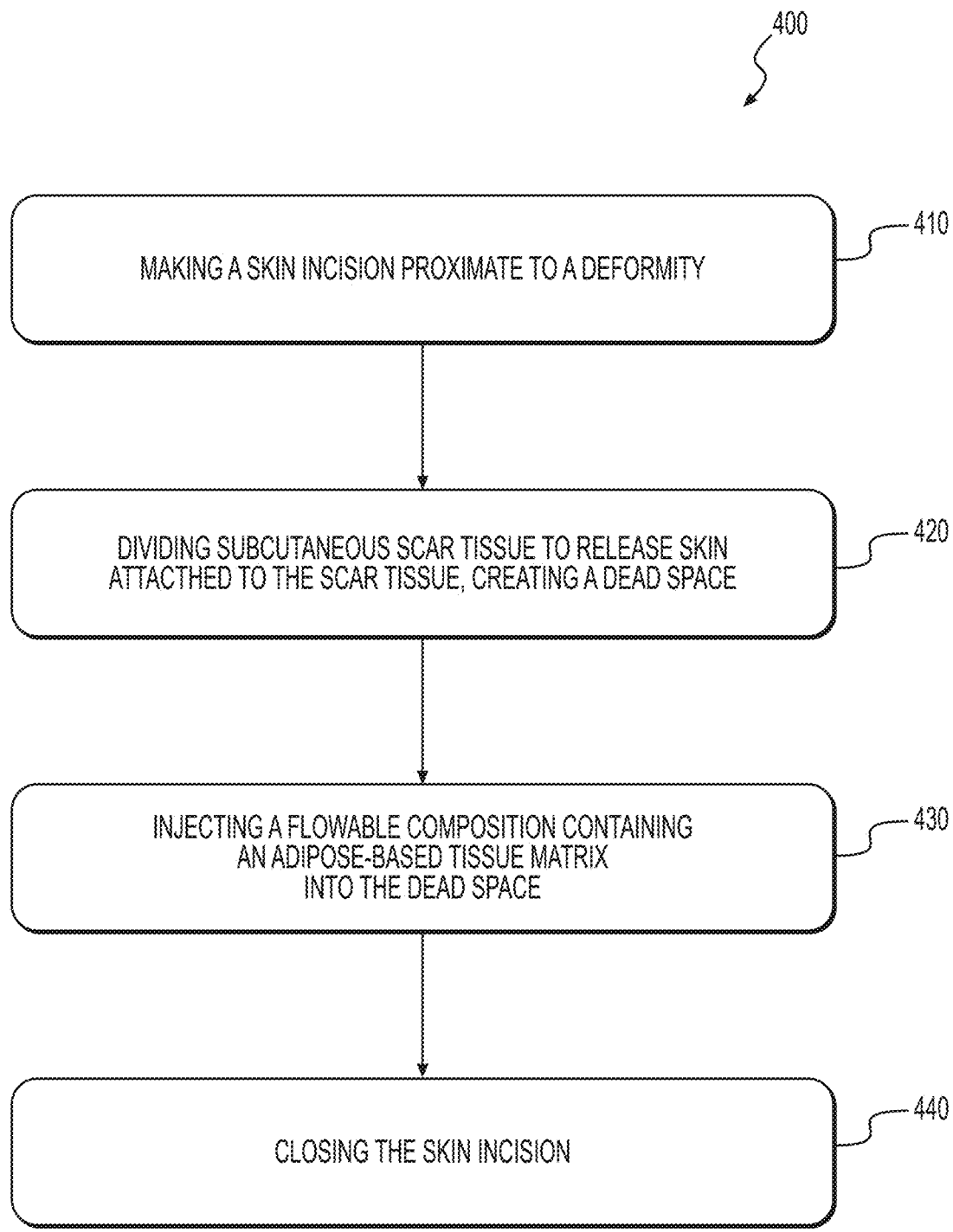
FIG. 19 is a flowchart outlining a process for repairing a skin deformity using a flowable adipose-based tissue matrix, according to embodiments of the present disclosure.

FIG. 19 is a flowchart outlining a process for repairing a skin deformity using a flowable adipose-based tissue matrix. FIG. 19 shows a method 400 comprising an incising step 410, a dividing step 420; an injecting step 430; and a closing step 440.

Incising step 410, in some embodiments, comprises incising the skin proximate to a deformity. A site for the skin incision is chosen according to the location, size, and severity of the defect. Often, it may be desirable to make the incision through non-deformed skin adjacent to the deformity. The skin incision may be a small 2-4 mm "stab" incision just large enough to accommodate a small pair of fine scissors or other instrument into the subcutaneous space. In some cases, it may be necessary to lengthen the incision. In some embodiments, the incision is made through the deformed skin. The procedure is typically done under local anesthesia, which is injected into the skin at the planned incision site, and into the subcutaneous tissue underlying the skin deformity. Use of a local anesthetic composition comprising epinephrine to aid with hemostasis may be desirable.

Dividing step 420, in some embodiments, comprises dividing subcutaneous scar tissue to release skin attached to the scare tissue, creating a dead space. A suitable instrument, such as a small pair of fine dissecting scissors or a long-handled scalpel is passed through the skin incision and used to cut through bands of scar tissue tethering the overlying skin, thereby releasing the scar tissue attachments to the overlying skin. After the deformed skin appears to be completely released from the underlying scar tissue, hemostasis can usually be obtained by direct pressure on the skin for a few minutes. If this is not effective, the incision may be lengthened and electrocautery or other means is used to secure hemostasis.

Injecting step 430, in some embodiments, comprises injecting a flowable composition containing an adipose-based tissue matrix into the dead space created by dividing step 420. Injecting step 430 is performed in a similar matter using similar devices as in delivering step 320 described herein above. A syringe is preferably used, however, because the incision is small and a slow, controlled delivery of the composition comprising the adipose-based tissue matrix allows the surgeon to watch the released skin become supported as the volume of injected composition increases. The surgeon can then decide, based on an anticipated volume loss of around fifteen percent (15%) as the adipose-based tissue matrix becomes incorporated into and largely replaced by the patients subcutaneous fat tissue over time.

Closing step 440, in some embodiments, comprises closing the skin incision. In many embodiments, the small stab incision made during incision step 410 can be closed with a single subcuticular ("deep") absorbable stitch. In some embodiments wherein a longer incision is necessary, closing step 440 is performed similarly to closing step 330 described herein above.

In some embodiments, it may be desirable to perform closing step 440 before injecting step 430. For example, following hemostasis after completing dividing step 420, closing step 330 is performed to close the incision and "seal" the wound. The unsupported skin at the site of the deformity will be seen to "sag." Injecting step 430 is then performed by injecting the flowable composition through a needle inserted percutaneously until the skin is fully supported, preferably with a slight excess rise above the surrounding skin to allow for volume loss as the adipose-based tissue matrix becomes incorporated in the patient's subcutaneous adipose tissue. By closing the incision before injecting the composition, no composition leaks out through the incision site before or during closing step 420

The following examples are presented to illustrate, but in no way limit, the present disclosure.

EXAMPLES

A. Production of Adipose Tissue Material

Figure 6:
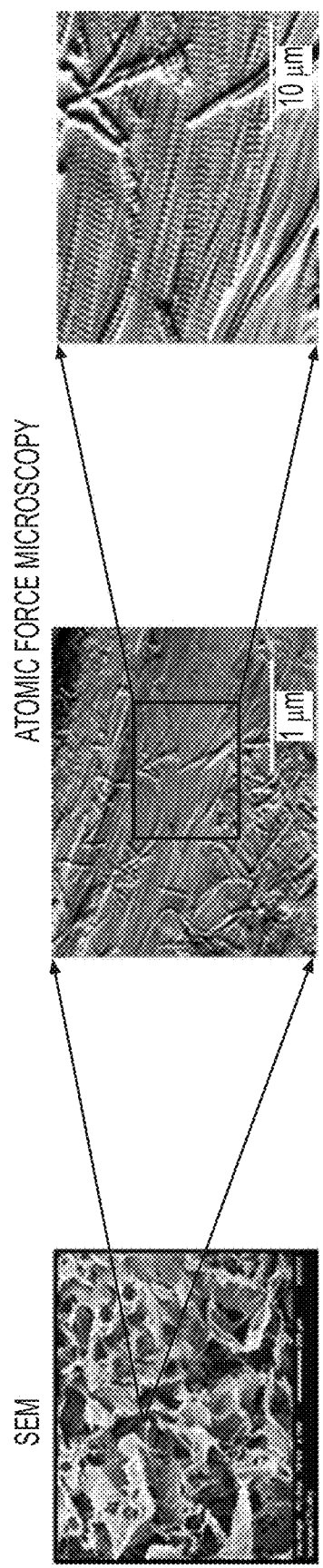
FIG. 6 illustrates scanning electron microscopy (SEM) and atomic force microscopy photos of adipose tissue matrix particles produced according to the process of the disclosed Examples.

To produce adipose tissue matrix materials, porcine fat tissue was first sliced into 2-inch strips and coarsely chopped in a food grade meat chopper. The chopped fat tissue may be frozen at −80° C., if not ready for further process. The frozen material may be thawed either at room temperature or 4° C. overnight. The preprocessed material was further coarse ground with RETSCH® GM300 (GRINDOMIX) at 2000 rpm, and then 4000 rpm, which provided for phase separation of oil from the solid matrix. The adipose matrix solid was harvested by centrifugation and washed with buffer. The matrix material was decellularized with an EDTA-Triton solution at room temperature overnight with one solution change at four hours. The matrix protein was subjected to washes again. During washing, the matrix pellet is centrifuged to pellet the tissue matrix and decant the used solution. The suspension was mechanically grinded again to further break down matrix fibers. After washing, the matrix pellet was resuspended in 20% PBS at a solid concentration of about ~2-3% w/w. The slurry was placed in a metal tray and was freeze dried to form a sponge and subject to DHT treatment to stabilize the material. The stabilized sponge was then ground and sieved to obtain a desired size of particles as flowable/injectable porcine acellular tissue slurry (PATS) material. The particulated material was made to a 5-15% paste and subjected to terminal sterilization by e-beam B. Process Produces Intact Collagen Structures The tissue product produced with the process described above was subjected to analysis with a Scanning Electron Microscope (SEM) and an Atomic Force Microscope (AFM). The results showed that the tissue product is a porous scaffold containing collagen materials with typical collagen banding pattern, including structure, porosity, etc., as shown in FIG. 6. The microscopy indicates intact collagen with normal banding patterns.

Figure 7A:
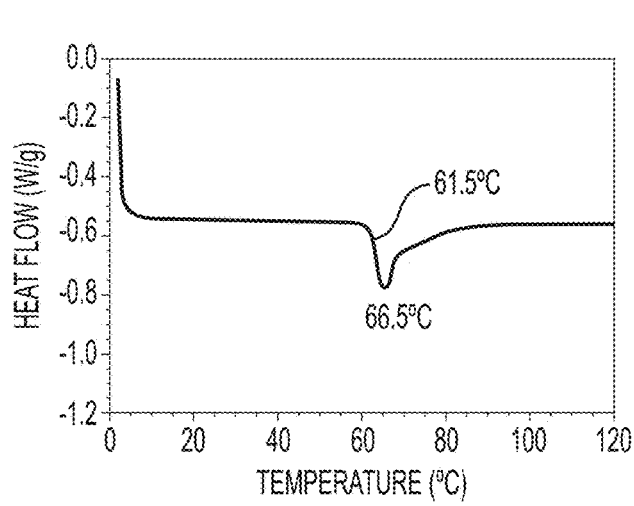
FIG. 7A illustrates differential scanning calorimetry curves for adipose tissue matrix material produced according to the disclosed Examples.

The tissue product was further subject to Differential Scanning calorimetry (DSC). The DSC results, as illustrated with reference to FIG. 7A, indicate that the tissue product has an onset melting temperature at 61.5° C. In this example, the tissue product's onset melting temperature was similar to native tissue (e.g., raw adipose).

Figure 7B:
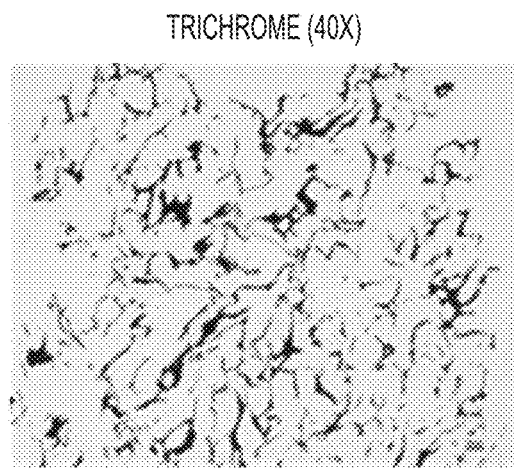
FIG. 7B is a Mason's trichrome stained section of adipose tissue matrix material produced according to the disclosed Examples.
Figure 7C:
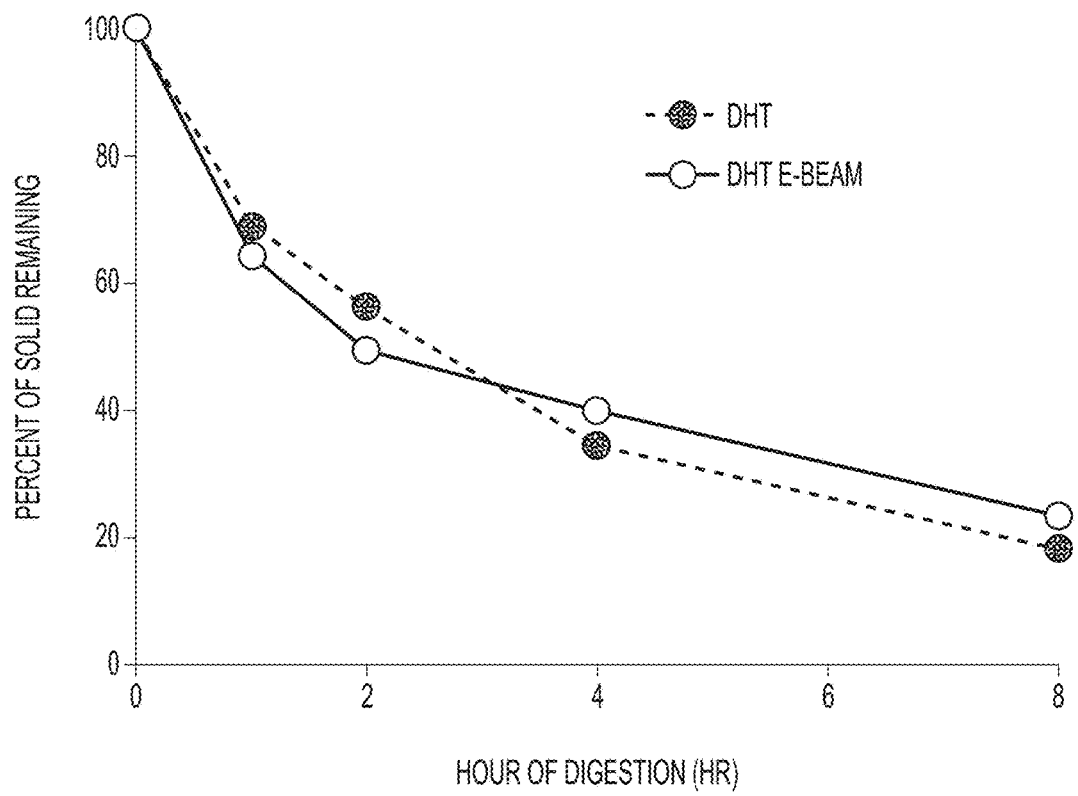
FIG. 7C illustrates collagenase digestion curves for adipose tissue produced according to the disclosed Examples, with or without e-beam sterilization.

The tissue was also subject to Mason's Trichrome staining and a collagenase digestion assay. Collagenase digestion was performed on tissue that was produced as described above with or without e-beam sterilization. The results of the staining and collagenase digestion are depicted by FIGS. 7B and 7C, respectively. Specifically, FIG. 7C depicts collagenase digestion curves for adipose tissue produced according to the disclosed Example—with and without e-beam sterilization. Without e-beam sterilization, and only DHT stabilization, the percentage of solid remaining as function of hours of digestion drops to approximately 18% after eight hours. With e-beam sterilization together with DHT stabilization, the percentage of solid remaining approaches about 25% after the same period of digestion, slightly higher than DHT only.

With continuing reference to FIGS. 7B and 7C, the material had Trichrome staining indicative of normal collagen on Trichrome section and unchanged collagenase susceptibility even after terminal sterilization by e-beam. Generally, when collagen is Trichrome stained, normal collagen should appear as blue with no red color. Taken together, the microscopy, DSC, staining, and collagenase digestion indicate preserved collagen.

C. Process Described is Efficient in Removal of Cells, Cell Remnants, and Oil in Scaffold The samples produced as described were also subject to hematoxylin and eosin staining ("H&E"), as depicted in FIG. 8A, DNA and lipid content analysis, as depicted in FIG. 8B, and immunostaining for MHC I and II components, as depicted in FIG. 8C (showing tissue matrix versus native fat control). On the H&E histology, the tissue product showed porous structure with no sign of cells. Consistent with this observation, the tissue product has significantly low residual DNA and free oil. By immunostaining, the tissue product is negative for MHC-1 & II staining, indicating the process described is efficient in decellularization.

D. Tissue Product Retained Major Matrix Components of Native Fat

Figure 9:
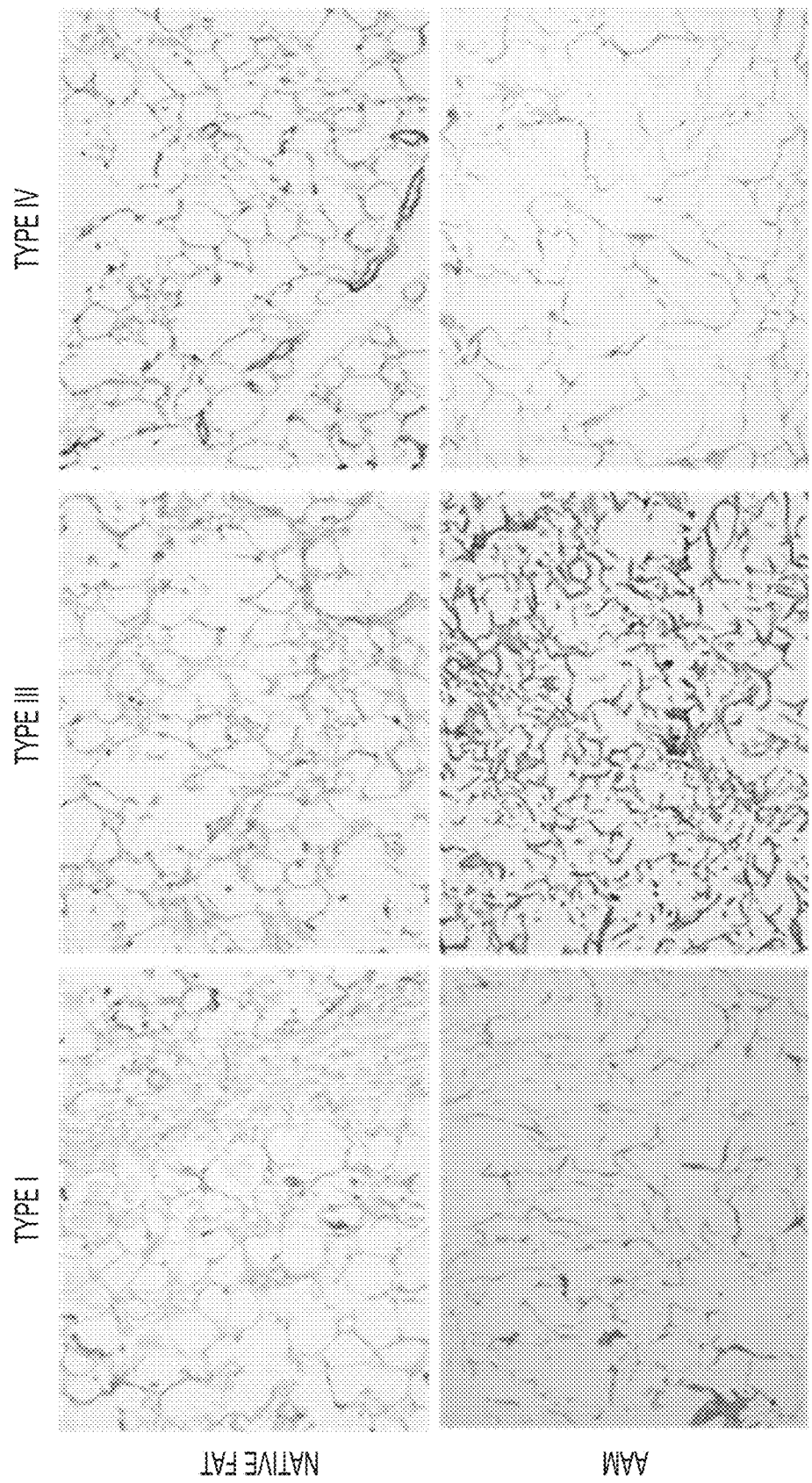
FIG. 9 provides histologic images of adipose tissue matrix produced according to the disclosed Examples as compared to native fat controls and subject to an immune-histological analysis for major extracellular matrix proteins (e.g., Type I, Type III, and Type IV) collagens.

The tissue was subject to immune-histological analysis for major extracellular matrix proteins including Type I, Type III and Type IV. With reference to FIG. 9, the adipose tissue product (lower row) preserved original characteristics of native adipose matrix (upper row).

E. Tissue Product Supports Multiple Tissue Cell Growth

Figure 10:
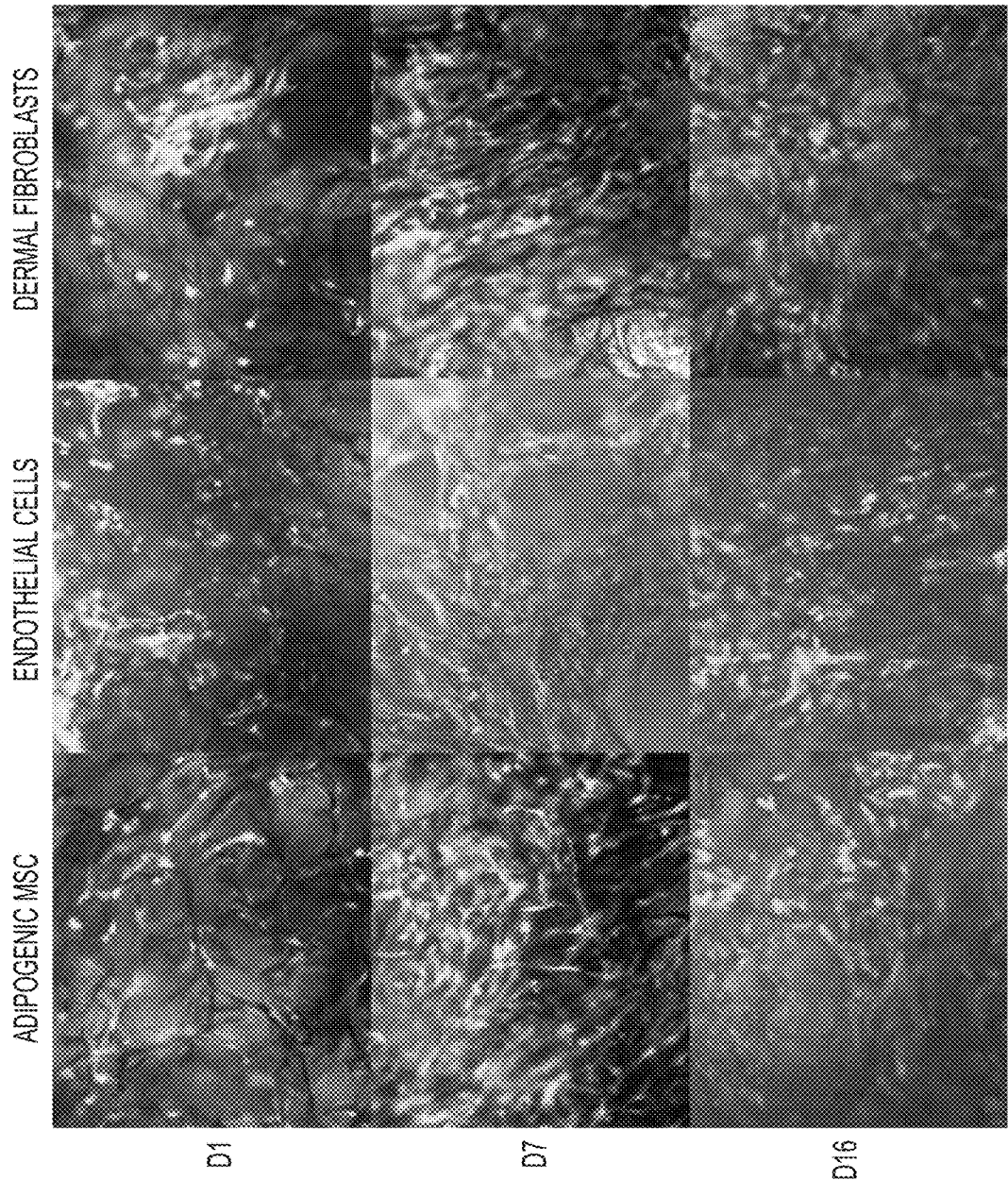
FIG. 10 provides light microscopic images of adipose tissue matrix produced according to the disclosed Examples supporting growth of three different cell types in vitro (e.g., adipogenic mesenchymal stem cells, endothelial cells, and dermal fibroblasts)

Three different cell types were chosen to test if the tissue product sponge has potential to support the growth of adipose tissue, vasculature, and other connective tissue like dermal tissue. Specifically, adipogenic mesenchymal stem cells, endothelial cells, and dermal fibroblasts, all primary cells isolated from normal humans individuals, were tested. The tissue product was seeded with cells isolated from these tissues and cultured for 1, 7, and 16 days. The cell growth was quantified with a cell proliferation assay kit. Using a CyQUANT® Cell Proliferation Assay Kit, the cell proliferation was quantified by DNA content using fluorescent dye. The tissue product was analyzed for cell growth. With reference to FIG. 10, the cell seeded scaffold was stained with live-dead staining solution and the viability and growth of cells were observed under fluorescent light microscopy. The tissue product supports all three types of cell growth in vitro.

F. Tissue Product Retained Volume and Supported Adipogenesis In Vivo

Figure 11:
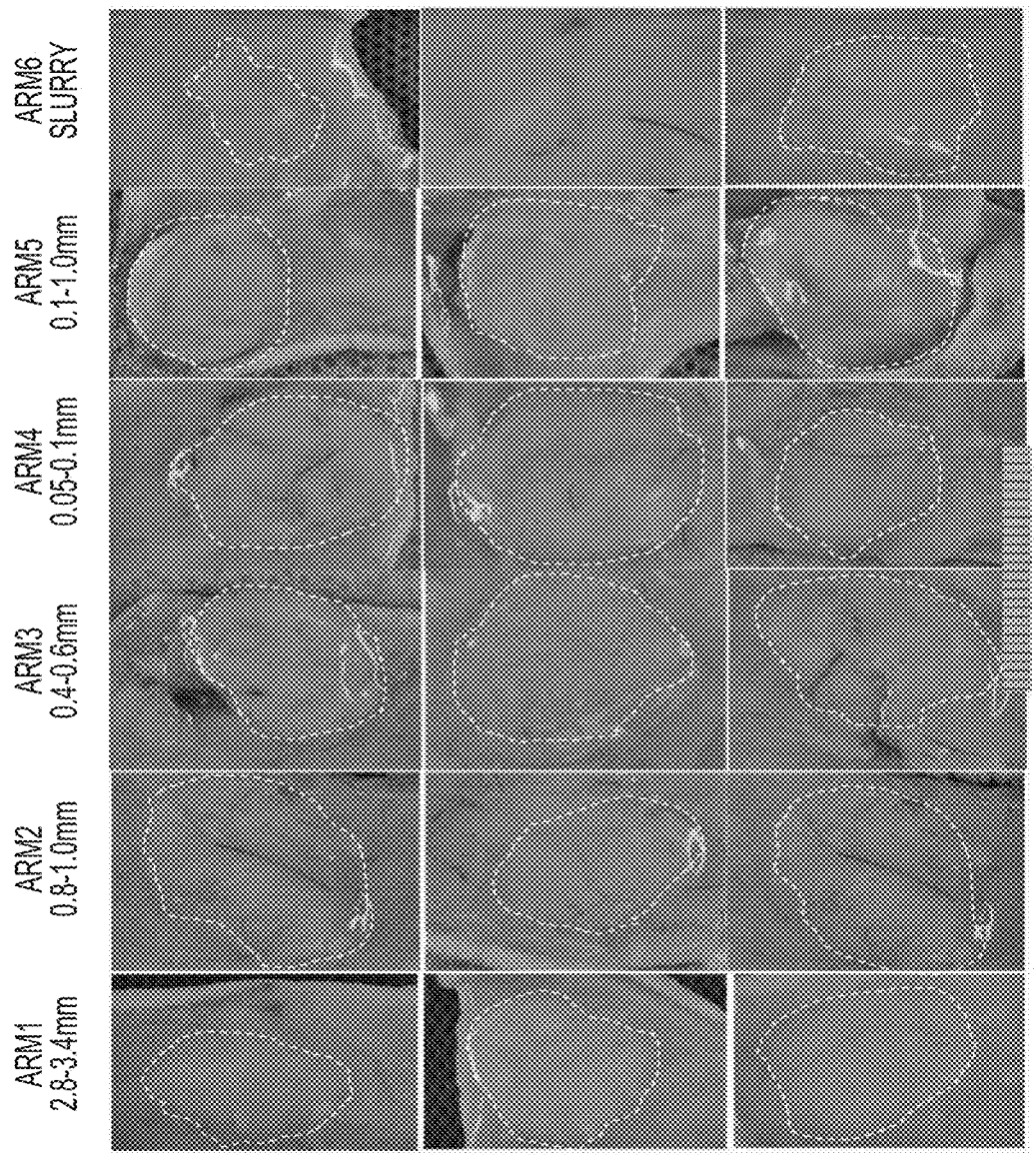
FIG. 11 provides gross photographs of explants of injectable adipose tissue matrix after subcutaneous implant in nude rats as prepared according to the enclosed Examples.

The biological performance of the product was tested in a subcutaneous nude rat model. As shown in FIG. 11, this study was designed to test different formulations of the product.

The product fabricated as described in Example A was grouped into five different size ranges: Arm 1: 2.8-3.4 mm; Arm 2: 0.8-1.0 mm; Arm 3: 0.4-0.6 mm; Arm 4: 0.05-0.1 mm; and Arm 5, 0.1-1 mm. A sixth Arm, Arm 6 included a slurry and fiber in nature that was the material obtained directly from after the decellularization process, without freeze drying and subsequent steps. Arm 6 was used as a control for comparison to the tissue product with DHT stabilized 3D microporous structures as in Arms 1-5. Arm 7 included a sponge prepared by a similar process, but from dermal acellular tissue matrix. The dermal tissue was Strattice®.

Arms 1-5 were first hydrated at 10% solid content by weight in normal saline to make injectable pastes, and Arm 6 was also similarly adjusted to 10% solid content. Arm 7 was a 10 mm punch in 5 mm thickness from a dermal sponge and hydrated in PBS. About 0.5 cc aliquot of each injectable adipose material (Arms 1-6), and the 10 mm punch of Arm 7, were implanted at the subcutaneous region of nude rats for triplicates of each arm.

At four weeks, explants were harvested for gross observation and were subject to a histological analysis. FIG. 11 illustrates gross observation of explants of injectable adipose tissue matrix after subcutaneous implant in nude rats. A dotted line indicates implanted material. All the explants were soft when palpated. Injectable adipose with all particle size ranges persisted for at least 4 weeks. It was also observed (data not shown) that injectable adipose implants with certain particle sizes persisted well for at least 12 weeks.

Figure 12:
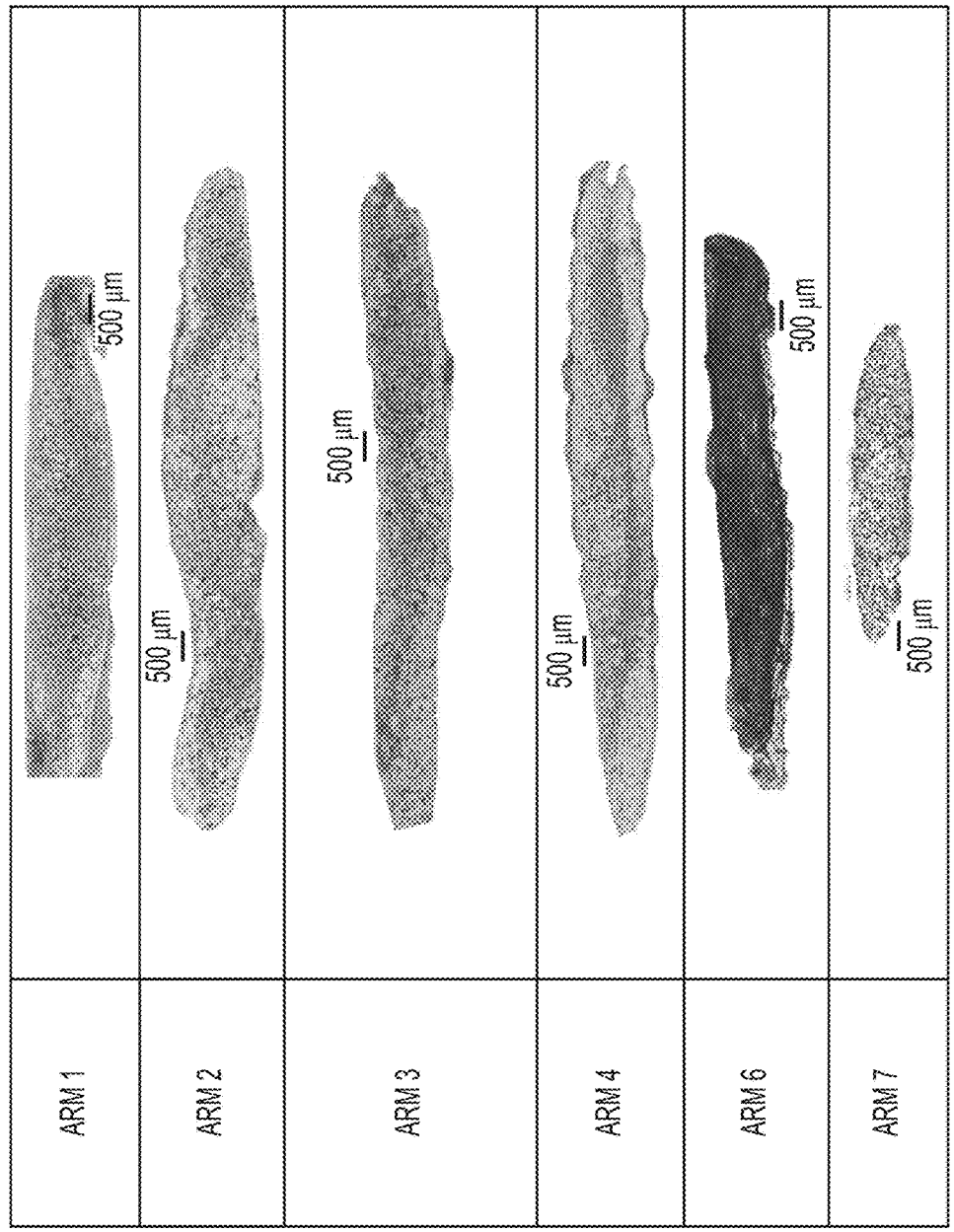
FIG. 12 illustrates Masson's Trichrome staining of the explants of injectable adipose tissue matrix after subcutaneous implant in nude rats as prepared according to the enclosed Examples.

FIG. 12 illustrates additional Masson's trichrome staining of the explants at lower magnification. A robust adipogenic response with tissue in-growth was observed for Arms 1-4 that were prepared from stabilized PATS sponges. In contrast, the adipose tissue matrix slurry of Arm 6, lacking any 3D structure (i.e., absence of freeze-drying and stabilization), elicited no adipogenic response (c).

Furthermore, Arm 7, as shown in FIG. 12, further illustrates an intact sponge-like porcine dermal tissue scaffold when implanted in the sub-cutaneous space of the same nude rat model. Masson's trichrome staining reveals no adipose tissue regeneration in the dermal scaffold, although volume was retained.

Figure 13:
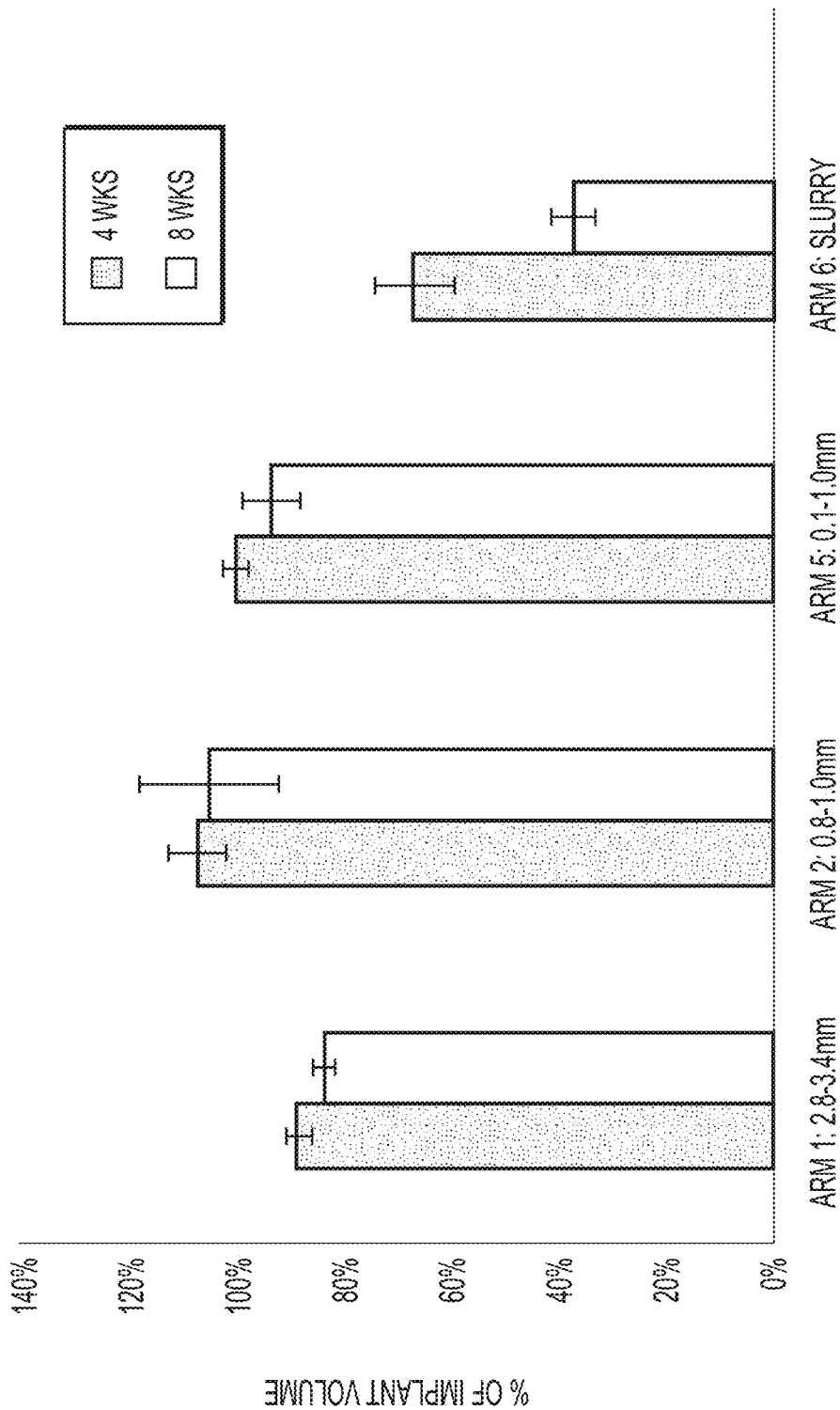
FIG. 13 is a bar graph illustrating explant volume remaining after rat subcutaneous implant for four or eight weeks, as described in the enclosed Examples.

The volume retention for the representative injectable adipose matrix products (Arm 1: 2.8-3.4 mm; Arm 2: 0.8-1.0 mm, Arm 5: 0.1-1.0 mm) along with the slurry of Arm 6 were also evaluated for 8 weeks as illustrated in FIG. 13. Arms 1, 2, and 5, all of which are particles with porous microstructures, retained more than 84% explants volume up to eight weeks when compared to the volume implanted.

Similar results would be expected for Arm 3: 0.4-0.6 mm and Arm 4: 0.05-0.1 mm since these arms had similar biological responses as Arms 1, 2 and 5 at 4 weeks. Microscopically, 0.4-0.6 mm particles have porous microstructure similar to that of Arms 1, 2 and 5. Although the 0.05-0.1 mm particles are too small to have intact micropores, most particles have branches and can form similar pores when in contact with each other due to the stabilized material with DHT (data not shown), which is fundamentally different from the slurry material in Arm 6. In contrast, implants with no micro-porous architecture, slurry form of adipose tissue (e.g., Arm 6) were either difficult to find or very flat when palpated; thus, indicating severe implant volume loss. The explants weight decreased over time and was only ~38% remained at the end eight weeks, indicating severe implant volume loss.

Figure 14A:
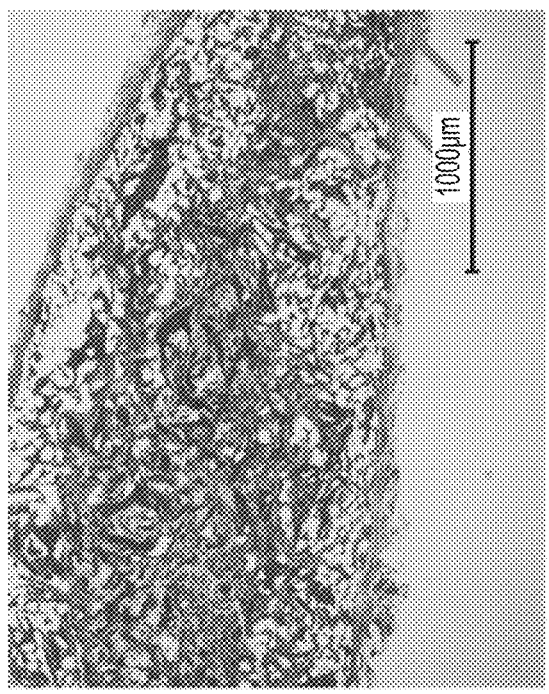
FIG. 14A is a Masson Trichrome stained section of eight week explants as described in the enclosed Examples.
Figure 14C:
FIG. 14C is another Masson Trichrome stained section of eight week explants as described in the enclosed Examples.
Figure 14B:
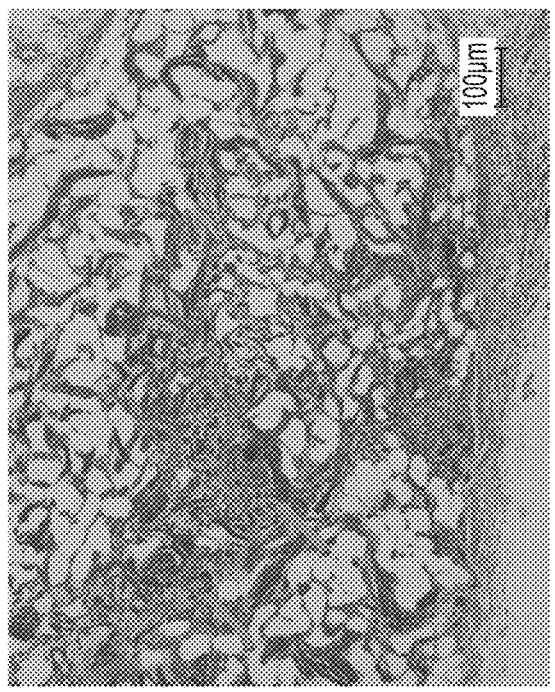
FIG. 14B is another Masson Trichrome stained section of eight week explants as described in the enclosed Examples.

FIGS. 14A-14C are zoomed-in Masson's Trichrome stained sections of explants from Arm 2, showing good adipogenesis. Adipocytes are white areas, which were plentiful and large; and vascularization was evident. Similar histologic findings were present with Arm 5 samples (not illustrated in the Figures).

Taken together, the results indicated that adipose tissue matrix particles in all sizes tested (e.g., 50 µm-3.4 mm) maintained volume, as illustrated in FIGS. 11 and 13, and had good cell infiltration and revascularization response up to eight weeks, data shown only at four weeks in FIG. 12. Whereas, in control Arm 6, a slurry from the same material prepared with the same process, but without being subject to freeze dry and DHT stabilization, had no adipose tissue in-growth response was observed in implant, as shown by Arm 6 in FIG. 12. Therefore, the results suggest that the micro-porous pore structure may be important or notable during adipogenesis, since Arm 6 lacks pore structures. In addition, Arm 6 suffered significant volume loss at the end of eight weeks (FIG. 13), which further indicates that DHT stabilization of the tissue product is important for volume retention in vivo. Furthermore, the adipose tissue in-growth is specific to the adipose matrix, and was absent in intact sponge-like scaffolds prepared with dermal acellular matrix using a similar process, as illustrated in Arm 7 of FIG. 12.

Figure 15:
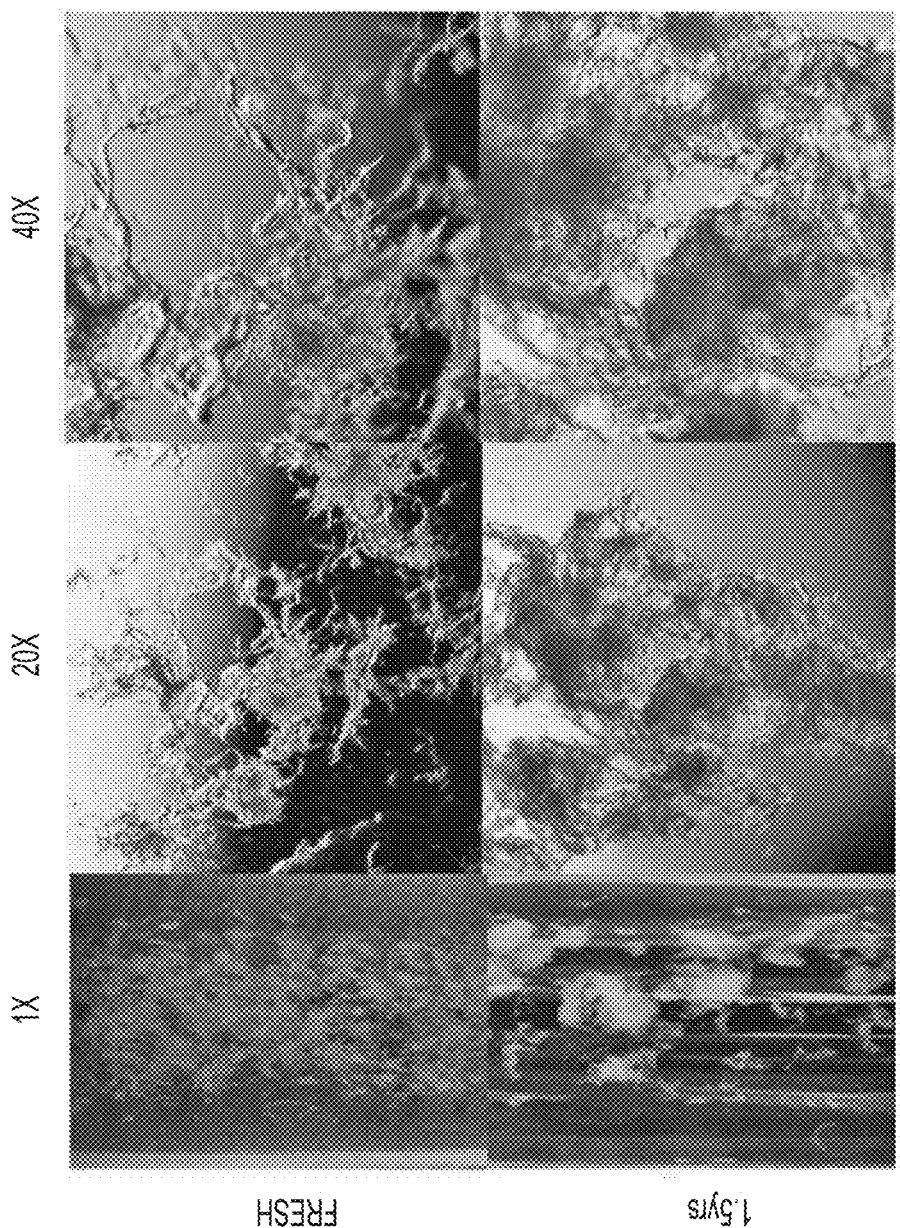
FIG. 15 provides microscopic images of aggregates formed in a wet adipose tissue matrix product after 1.5 years of storage

G. Using Hyaluronic Acid (HA) as a Carrier Increased Injectability of Adipose Tissue Product FIG. 15 provides images of fresh adipose tissue matrix, as compared to tissue matrix stored for 1.5 years, both of which were prepared as described in Example A. The images are provided at various magnifications. As illustrated, an adipose tissue matrix material in a wet format containing 10% solid formed aggregates after 1.5 years of storage. Biologic tests indicate that the aggregation does not impact biological performance of the material such as volume retention and adipose tissue in-growth in the subcutaneous region of nude rat. However, for non-invasive delivery at a clinical setting, the 10% adipose tissue product may require a carrier to facilitate Injectability.

To facilitate the injectability of the adipose tissue material, a 20 mg/mL, non-crosslinked hyaluronic acid (HA) carrier was mixed with either a freshly prepared adipose tissue matrix (10%, 0.1-1.0 mm) or a 1.5-year-old adipose tissue matrix (10%, 0.1-1 mm). The final concentration of the HA additive in the mixed material was 2 mg/mL. The compressive load (N) required for injection of the adipose material, with or without the HA additive was evaluated on an Instron Model 5865 materials tester (Instron Corporation, Norwood, Mass.). The adipose material without HA was injected through either a 16 G needle or an 18 G needle, and the adipose material with HA additive was injected through an 18 G needle. The mean compressive forces over time for the product with or without HA additive (n=3) were calculated and plotted.

As depicted in Table 2, without HA as a carrier, the injection of the fresh adipose material using a 16 G needle was smooth, but the 1.5-year-old adipose encountered significant resistance. Upon the addition of HA as a carrier, both fresh adipose material and 1.5-year-old material became injectable.

TABLE 2

| | Injectability | |
|---|---|---|
| Product Age | w/o HA (16G) | HA (2 mg/mL final concentration) (18G) |
| Fresh | Smooth (<50N) | Smooth (<50N) |
| 1.5 yrs Old | Not Injectable | Smooth (<50N) |

Figure 16:
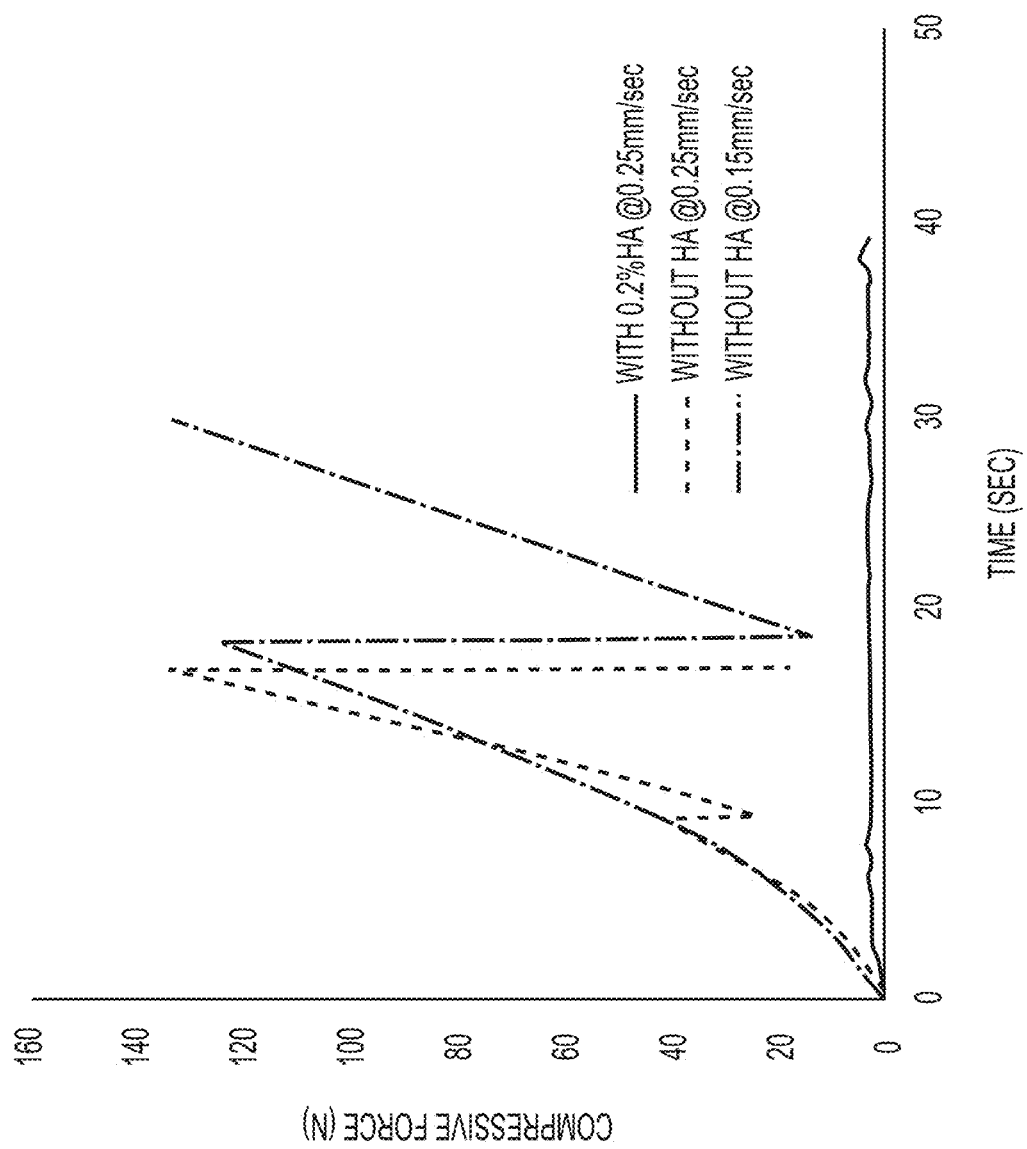
FIG. 16 is a graph of injection force for adipose matrix products with or without HA as a flowable carrier.

As depicted in FIG. 16, without HA as a carrier, the injection of a freshly prepared adipose material at both 0.15 mm/sec and 0.25 mm/sec speed, encountered significant resistance through an 18 G needle, while the injection of the product with 2 mg/mL HA additive (final concentration), even at a 0.25 mm/sec speed, became extremely smooth.

Figure 17:
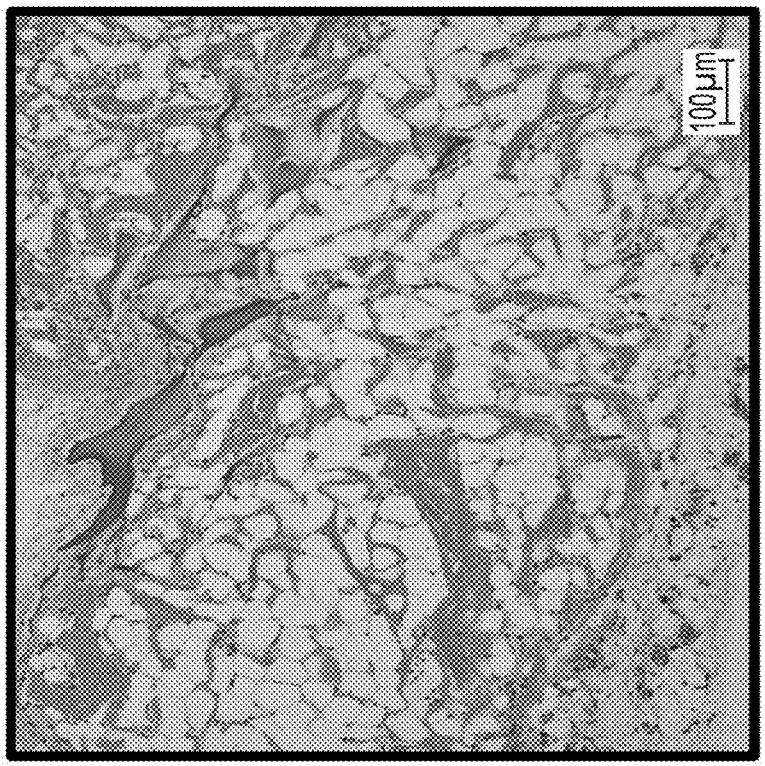
FIG. 17 is an H&E stained section of a four-week HA-adipose explant as described in the Examples.

To evaluate the biological performance of the mixture of adipose product with HA additive, a 1:10 ratio of 20 mg/mL, cross-linked hyaluronic acid (HA Type 4) and the adipose tissue matrix (10%) were mixed, and the mixture was injected into the subcutaneous region of a nude rat. An explant of the HA-adipose product mixture was harvested 4 weeks after the injection and as depicted in FIG. 17, a robust adipose tissue ingrowth was observed in the explant.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

Example H

Longer-Term Implantation Study

Figure 20:
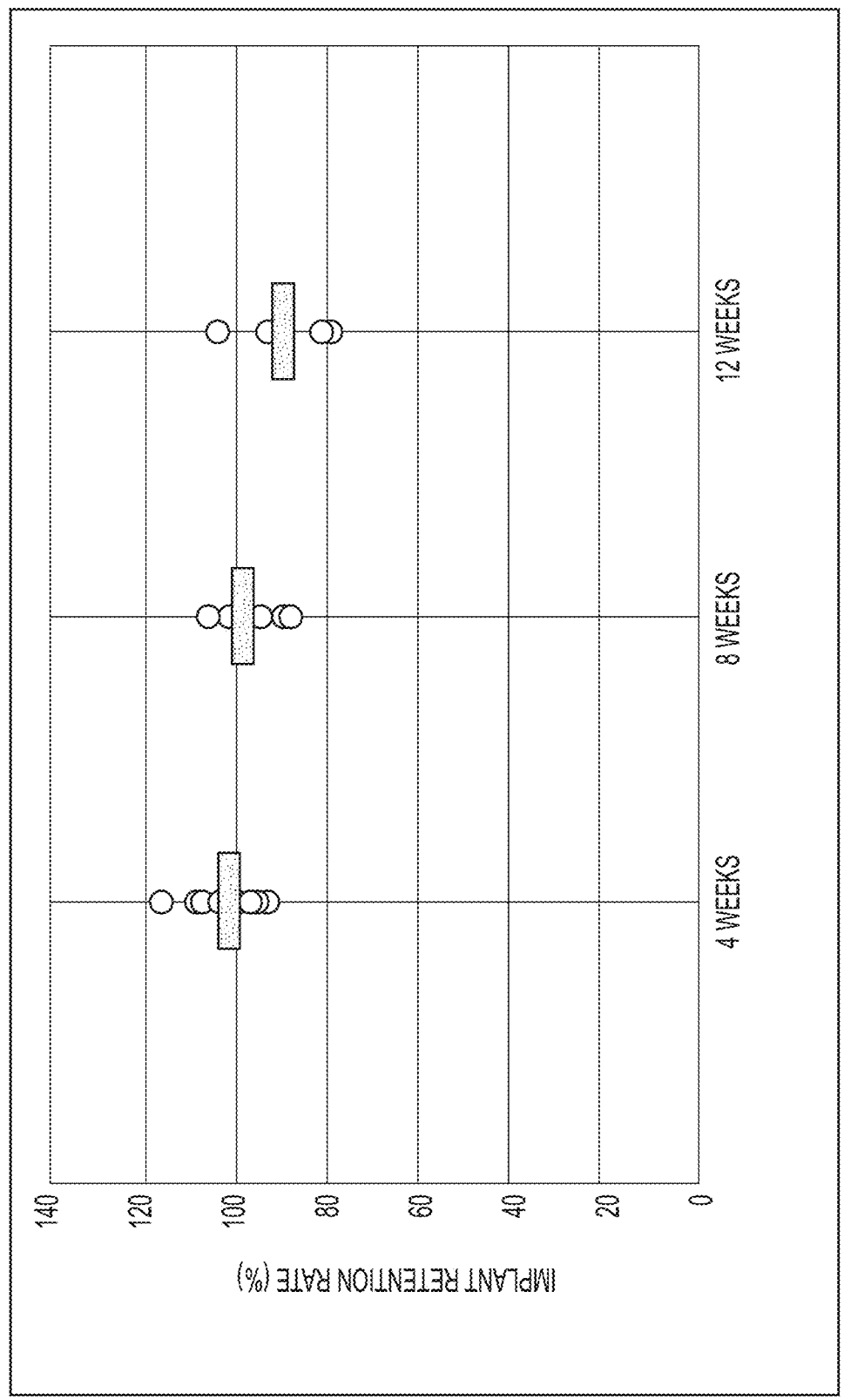
FIG. 20 is a graph illustrating volume retention of an adipose matrix composition implanted subcutaneously for up to twelve weeks, according to the disclosed Examples.

To test longer term volume retention, ARM 5 of Example F was implanted in the same subcutaneous model. FIG. 20 is a graph illustrating volume retention of an adipose matrix composition implanted subcutaneously for up to twelve weeks, according to the disclosed Examples. As shown, the adipose matrix maintains up to 90% volume even at twelve weeks.

Example I

Acute and Chronic Wound Model Improvement Using Adipose Tissue Matrix

To evaluate the effect of adipose matrix in soft tissue repair, two types of subcutaneous defect wounds were created in Yucatan mini-swine, the Chronic Defect Wound (CDW) model and Acute Defect Wound (ADW) model.

After animals were sedated, three (3) circular full thickness skin flaps of 3 cm in diameter (with approximately half of the wound border left intact) were created at the site of each wound on the dorsum along each side of the spinal cord, a total of six wound sites generated. The six paraspinal tunnel wounds were created underneath each skin flap with a 2 cm diameter custom circular biopsy instrument to dissect away an approximate 2 cm in diameter×4 cm long cylindrical defect encompassing subcutaneous tissue till the deep muscle layer.

For CDW model, after the wound defects were created on Day −4, the wounds further received thermal injury to delay an acute wound healing process. On Day 0 after 4 days post wound creation, the wound defects were surgically debrided and then treated with or without 10% adipose matrix product. The adipose product was prepared as described in Example A with particles in the range of 1-3 mm. The adipose matrix For ADW model, the wound defects were created on Day 0 and were immediately treated with or without 10% adipose matrix product. Animals for each model were terminated 14- and 28-days post implantation.

On both necropsy days, after animals were euthanized, each entire wound was excised with at least 2 cm of surrounding tissue attached. Gross observation of each wound and surrounding tissue was performed to evaluate wound healing with different treatments in CDW or ADW models, followed by histology evaluation.

If the defect was left empty, the wound edges approached to each other at as early as 14 days during healing in both acute (FIG. 21A) and chronic wound defects (FIG. 22A), with chronic wound presence of severe seroma and thickening wound edges (FIG. 22). The acute wound progressed to closure on Day 28 (FIG. 21B) by continuously pulling the wound margins toward the center of the wound, resulting in severe contraction, while the contracted wound was still partially open with yellowish gel around wound edges in the empty defect of CDW model (FIG. 22B), which is the residual seroma observed on Day 14.

In contrast, the defect treated with adipose matrix particles showed no contraction on Day 14 in ADW model (FIG. 21C) and no seroma and less contraction in CDW model (FIG. 22C). The defect space in both models was maintained by the adipose matrix filler with little deformity in surrounding tissue. On Day 28, the adipose matrix appeared similar in color and texture to the host tissue (FIGS. 21D and 22D), indicating tissue remodeling within the implant over time. There was no contraction around the defect wound like the observation on Day 14.

Historically the explant showed progressive fibroblast cell infiltration and robust vascularization from 14 to 28 days (data not shown), while the empty defects had significant granuloma formation.

Collectively, these data suggest that the adipose matrix is a promising filler for deep wound healing through regeneration while prevention of scar formation (no seroma, no contraction), thereby minimizing or eliminating the need for more extensive surgical revision in "hard-to-heal" wounds.

What is claimed is:

1. A method for treating a void in soft tissue comprising:
   removing an implanted infusion port from an anatomic location of a subject to create a void through a skin incision;
   delivering a flowable composition comprising an adipose-based tissue matrix into the void at a time proximate to the removing step; and
   closing the skin incision.

2. The method of claim 1, wherein the composition is delivered before closing the incision.

3. The method of claim 1, wherein the composition is delivered after closing the incision.

4. The method of claim 1, wherein the anatomic location is an anterior chest wall.

5. The method of claim 1, wherein the delivering step comprises injecting the flowable composition through a needle inserted percutaneously.

6. The method of claim 1, wherein the delivering step comprises placement of the composition into the void through an open surgical incision.

7. The method of claim 1, wherein the composition comprises a carrier that prevents dissipation of the adipose-based tissue matrix away from the void.

8. The method of claim 1, wherein the composition further comprises a glycosaminoglycan.

9. The method of claim 8, wherein the glycosaminoglycan is hyaluronic acid.

10. The method of claim 9, wherein the hyaluronic acid is a non-crosslinked hyaluronic acid.

11. The method of claim 9, wherein the hyaluronic acid is a crosslinked hyaluronic acid.

12. The method of claim 9, wherein the hyaluronic acid is present in the composition at a concentration by weight of about 2.5%.

13. The method of claim 1, wherein the composition comprises a local anesthetic.

14. The method of claim 1, wherein the adipose-based tissue matrix is in the form of a suspension of tissue particles having a longest dimension no greater than about 3.0 mm.

15. The method of claim 1, wherein the adipose-based tissue matrix is in the form of a suspension of tissue particles having a longest dimension of at least 0.05 mm.

16. The method of claim 1, wherein the adipose-based tissue matrix is in the form of a suspension of tissue particles having a longest dimension between about 100 μm and about 300 μm.

17. The method of claim 1, wherein the adipose-based tissue matrix is in the form of a suspension of tissue particles having a longest dimension between about 50 μm and about 100 μm.

18. The method of claim 1, wherein the delivering step comprises injection of the composition through at least one of a syringe, a cannula, or a needle.

19. The method of claim 1, wherein the delivering step comprises positioning the composition by manual insertion using at least one of a hand, a spatula, or a tube configured to handle flowable materials.

* * * * *